(12) United States Patent
Reich et al.

(10) Patent No.: US 11,617,652 B2
(45) Date of Patent: *Apr. 4, 2023

(54) APPARATUS AND METHOD FOR GUIDE-WIRE BASED ADVANCEMENT OF AN ADJUSTABLE IMPLANT

(71) Applicant: Edwards Lifesciences Innovation (Israel) Ltd., Caesarea (IL)

(72) Inventors: Tal Reich, Moledet (IL); Eran Miller, Moshav Beit Elazari (IL); Tal Sheps, Givat Shmuel (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 404 days.

This patent is subject to a terminal disclaimer.

(21) Appl. No.: 17/001,566

(22) Filed: Aug. 24, 2020

(65) Prior Publication Data
US 2020/0383787 A1 Dec. 10, 2020

Related U.S. Application Data

(60) Continuation of application No. 15/970,743, filed on May 3, 2018, now Pat. No. 10,751,184, which is a
(Continued)

(51) Int. Cl.
*A61F 2/24* (2006.01)
*A61B 17/04* (2006.01)
*A61B 17/00* (2006.01)

(52) U.S. Cl.
CPC ........ *A61F 2/2457* (2013.01); *A61B 17/0401* (2013.01); *A61F 2/2445* (2013.01);
(Continued)

(58) Field of Classification Search
CPC .... A61F 2/2457; A61F 2/2466; A61F 2/2445; A61F 2/2487; A61F 2220/0016;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 113331995 A 9/2021
EP 1034753 A1 9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Katherine M Shi
(74) *Attorney, Agent, or Firm* — Thomas C. Richardson

(57) ABSTRACT

A tissue-engaging element has a distal portion configured to engage a portion of tissue of the heart. A guide member is reversibly coupled to the tissue-engaging element. An elongate implant has a distal end and a proximal end, at least the distal end being slidably coupled to the guide member. A tool is slidable along the guide member distally toward the tissue-engaging element while (i) the tool is coupled to at least the distal end of the elongate implant, and (ii) the guide member is coupled to the tissue-engaging element, such that sliding of the tool along the guide member distally toward the tissue-engaging element while (i) the tool is coupled to at least the distal end of the elongate implant, and (ii) the guide member is coupled to the tissue-engaging element, slides at least the distal end of the elongate implant toward the tissue-engaging element.

20 Claims, 17 Drawing Sheets

Related U.S. Application Data division of application No. 14/937,233, filed on Nov. 10, 2015, now Pat. No. 9,968,454, which is a continuation of application No. 13/707,013, filed on Dec. 6, 2012, now Pat. No. 9,180,007, which is a continuation-in-part of application No. PCT/IL2011/000446, filed on Jun. 6, 2011, and a continuation-in-part of application No. 12/795,192, filed on Jun. 7, 2010, now Pat. No. 8,690,939, and a continuation-in-part of application No. 12/795,026, filed on Jun. 7, 2010, now Pat. No. 8,940,042, which is a continuation-in-part of application No. 12/608,316, filed on Oct. 29, 2009, now Pat. No. 8,277,502.

(52) U.S. Cl.
CPC .......... *A61F 2/2466* (2013.01); *A61F 2/2487* (2013.01); *A61B 2017/00243* (2013.01); *A61B 2017/00783* (2013.01); *A61B 2017/0441* (2013.01); *A61B 2017/0448* (2013.01); *A61B 2017/0464* (2013.01); *A61B 2017/0496* (2013.01); *A61F 2250/0007* (2013.01)

(58) Field of Classification Search
CPC ......... A61F 2250/0007; A61B 17/0401; A61B 2017/00243; A61B 2017/0464; A61B 2017/0496; A61B 2017/0409
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,501,683 A | 3/1996 | Trott |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,782,862 A | 7/1998 | Bonutti |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |

(56) References Cited

U.S. PATENT DOCUMENTS

| | | |
|---|---|---|
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |

(56) References Cited

U.S. PATENT DOCUMENTS

| | | |
|---|---|---|
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095139 A1 | 7/2002 | Keogh et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |

(56) References Cited

U.S. PATENT DOCUMENTS

| | | |
|---|---|---|
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1 | 11/2003 | Chu |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Saiahieh et al. |
| 2005/0137695 A1 | 6/2005 | Saiahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0245821 A1 | 11/2005 | Govari et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |

(56) References Cited

U.S. PATENT DOCUMENTS

| | | |
|---|---|---|
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0265491 A1 | 11/2007 | Krag et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0082132 A1 | 4/2008 | Annest et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stabler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0187216 A1 | 7/2009 | Schmieding et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1 | 6/2010 | Maisano et al. |
| 2010/0161043 A1 | 6/2010 | Maisano et al. |
| 2010/0161047 A1* | 6/2010 | Cabiri .................. A61B 17/068 623/2.37 |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280605 A1 | 11/2010 | Hammer et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0288635 A1 | 11/2011 | Miller et al. |
| 2011/0301498 A1 | 12/2011 | Maenhout et al. |
| 2012/0022557 A1 | 1/2012 | Cabiri et al. |
| 2012/0022644 A1 | 1/2012 | Reich et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |

(56) References Cited

U.S. PATENT DOCUMENTS

| | | |
|---|---|---|
| 2012/0078359 A1 | 3/2012 | Li et al. |
| 2012/0083806 A1 | 4/2012 | Goertzen |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0203332 A1 | 8/2012 | Navia et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096672 A1 | 4/2013 | Reich et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0119905 A1 | 4/2015 | Shluzas et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0121033 A1 | 5/2016 | Cotter et al. |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0000611 A1 | 1/2017 | Gilmore et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2022/0096232 A1 | 3/2022 | Skaro et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |

(56) References Cited

FOREIGN PATENT DOCUMENTS

| | | |
|---|---|---|
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spillner, and Th Johannesson, "Hemodynamic changes following experimental production and correction of acute mitral regurgitation with an adjustable ring prosthesis." The Thoracic and cardiovascular surgeon36.06 (1988): 313-319.
Ahmadi, Ali et al. "Percutaneously adjustable pulmonary artery band." The Annals of thoracic surgery 60 (1995): S520-S522.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri et al., "The edge to edge technique," The European Association for Cardio-Thoracic Surgery 14th Annual Meeting Oct. 7-11, Book of Procees. (2000).
Alfieri et al."Novel Suture Device for Beating-Heart Mitral Leaflet Approximation", Ann Thorac Surg. 2002, 74:1488-1493.
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
Amplatzer® Cribriform Occluder. A patient guide to Percutaneous, Transcatheter, Atrial Septal Defect Closuer, AGA Medical Corporation, Apr. 2008.
Amplatzer® Septal Occluder. A patient guide to the Non-Surgical Closuer of the Atrial Septal Defect Using the Amplatzer Septal Occluder System, AGA Medical Corporation, Apr. 2008.
Assad, Renato S. "Adjustable Pulmonary Artery Banding." (2014).

Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence, investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

APPARATUS AND METHOD FOR GUIDE-WIRE BASED ADVANCEMENT OF AN ADJUSTABLE IMPLANT

CROSS-REFERENCES TO RELATED APPLICATIONS

The present application is a Continuation of U.S. Ser. No. 15/970,743 to Reich et al., which published as US 2018/0250133, which is a Divisional of U.S. Ser. No. 14/937,233 to Reich et al., now U.S. Pat. No. 9,968,454, which is a continuation of U.S. Ser. No. 13/707,013 to Reich et al., now U.S. Pat. No. 9,180,007, which is a continuation-in-part of:

a. International Application PCT/IL2011/000446 to Miller et al., entitled "Apparatus and method for guide-wire based advancement of a rotation assembly," filed on Jun. 6, 2011 (which published as WO/2011/154942);

b. U.S. patent application Ser. No. 12/795,192 to Miller et al., entitled "A method for guide-wire based advancement of a rotation assembly," filed on Jun. 7, 2010 (which published as US 2011/0301698) (now U.S. Pat. No. 8,690,939); and c. U.S. patent application Ser. No. 12/795,026 to Miller et al., entitled "Apparatus for guide-wire based advancement of a rotation assembly," filed on Jun. 7, 2010 (which published as US 2011/0106245, now U.S. Pat. No. 8,940,042), which is a continuation-in-part of U.S. patent application Ser. No. 12/608,316 to Miller et al., entitled, "Tissue anchor for annuloplasty device," filed on Oct. 29, 2009 (now U.S. Pat. No. 8,277,502).

All of these applications are incorporated herein by reference.

FIELD OF THE INVENTION

The present invention relates in general to valve and chordeae tendineae repair. More specifically, the present invention relates to repair of an atrioventricular valve and associated chordeae tendineae of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

SUMMARY OF THE INVENTION

In some applications of the present invention, apparatus is provided comprising an implant comprising one or more primary adjustable repair chords and an adjustment mechanism that is configured to adjust a tension of the one or more adjustable repair chords and that is slidable along a guide wire toward an implantation site. Additionally, the apparatus comprises a first tissue-engaging element (e.g., a tissue anchor) that comprises one or more docking stations. Further additionally, in accordance with some applications of the present invention, a method is provided for implanting such apparatus. A respective guide wire is reversibly coupled to each one of the docking stations. The adjustment mechanism is slidable along the guide wire toward one of the one or more docking stations, and is coupled to the tissue-engaging element via the docking station. Thus, the docking station is a coupling element that provides coupling between two other elements (in this case, between adjustment mechanism and the tissue-engaging element.)

The repair chord comprises a flexible, longitudinal member (e.g., sutures or wires). The repair chord is coupled at a distal portion thereof to the adjustment mechanism. In some applications, the repair chord functions as artificial chordae tendineae. In other applications, the repair chord is used to adjust a distance between two portions of the ventricular wall. For some applications, the repair chord is coupled at a proximal portion thereof to a second tissue-engaging element (e.g., a tissue anchor which penetrates or clips a portion of tissue).

For other applications, the repair chord comprises a cord that is disposed within at least a portion of an annuloplasty ring structure (e.g., a full annuloplasty ring or a partial annuloplasty ring). For such applications, the annuloplasty ring structure comprises the adjustment mechanism that is coupled to the repair cord. The annuloplasty ring structure is slidable along the guide wire toward one of the one or more docking stations, and is coupled to the tissue-engaging element via the docking station. It is to be noted that the annuloplasty ring structure may be provided independently of the adjustment mechanism and the repair chord. For such applications, the annuloplasty ring structure is slidable along the guide wire toward one of the one or more docking stations, and is coupled to the tissue-engaging element via the docking station.

For yet other applications, a prosthetic heart valve and/or a support for the prosthetic heart valve is slidable along the guide wire toward one of the one or more docking stations, and is coupled to the tissue-engaging element via the docking station.

Thus, the tissue-engaging element and the docking station are used to facilitate implantation of an implant such as cardiac valve implants, namely annuloplasty ring structures, prosthetic valves, and/or apparatus for receiving a prosthetic valve (e.g., a docking station or a support for receiving the prosthetic valve).

Typically, during a transcatheter procedure, the first tissue-engaging element is coupled to a first portion of tissue at a first implantation site in a heart of a patient. The adjustment mechanism is then slid along the guide wire and toward the first tissue-engaging element at the first implantation site. The proximal portion of the repair chord is then coupled via the second tissue-engaging element to a second portion of tissue at a second implantation site. Following the coupling of the second tissue-engaging element to the second implantation site, the adjustment mechanism is further slid distally toward the first tissue-engaging element and is then coupled to the first tissue-engaging element via the one or more docking stations on the first tissue-engaging element. Following the coupling of the adjustment mechanism to the second tissue-engaging element, a length and tension of the repair chord is then adjusted in order to adjust a distance between the first and second implantation sites. For applications in which the repair chord functions as an artificial chordea tendinea, the adjustment of the length and tension of the repair chord draws the leaflets together, and/or pulls the leaflet down toward the first implantation site to repair the valve.

In some applications of the present invention, the adjustment mechanism comprises a spool assembly which adjusts a degree of tension of the repair chord. The spool assembly comprises a housing, which houses a spool to which a distal portion of the repair chord is coupled.

For applications in which the repair chord is coupled to two respective portions of the ventricular wall, the two portions are drawn together, thereby restoring the dimensions of the heart wall to physiological dimensions, and drawing the leaflets toward one another.

In some applications of the present invention, the adjustment mechanism comprises a reversible locking mechanism which facilitates bidirectional rotation of the spool in order to effect both tensioning and relaxing of the repair chord. That is, the spool is wound in one direction in order to tighten the repair chord, and in an opposite direction in order to slacken the repair chord. Thus, the spool adjustment mechanism facilitates bidirectional adjustment of the repair chord.

In some applications of the present invention, the adjustable repair chord is implanted during an open-heart or minimally-invasive procedure. In these applications, the delivery tool comprises a handle and a multilumen shaft that is coupled at a distal end thereof to the adjustment mechanism. The delivery tool functions to advance the adjustment mechanism to the first portion of tissue, implant the adjustment mechanism at the first portion of tissue, and effect adjustment of the repair chord by effecting rotation of the spool. For applications in which the repair chord functions as an artificial chordea tendinea, prior to implantation of the adjustment mechanism, the distal portion of the delivery tool and the adjustment mechanism coupled thereto are advanced between the leaflets of the atrioventricular valve and into the ventricle toward the first portion of tissue. The incision made in the heart is then closed around the delivery tool and the heart resumes its normal function during the adjustment of the length of the artificial chordea tendinea.

In some applications of the present invention, apparatus and method described herein may be used for providing artificial chordae tendineae in a left ventricle of the heart and effecting adjustment thereof. In some applications, apparatus and method described herein may be used for providing artificial chordae tendineae in a right ventricle of the heart and effecting adjustment thereof. In some applications, apparatus and method described herein may be used for providing a system to adjust a length between two portions of the heart wall. For other applications apparatus and method described herein may be used for providing a docking station for an annuloplasty ring or for a prosthetic valve.

There is therefore provided, in accordance with an application of the present invention, apparatus, including:
a guide member;
a tissue-adjustment mechanism having:
an upper surface and a lower surface,
at least one first opening at the upper surface,
at least one second opening at the lower surface, and
a channel extending between the first and second openings, the channel facilitating advancement of the tissue-adjustment mechanism along the guide member; and
at least one repair chord coupled at a first portion thereof to the tissue-adjustment mechanism and having at least a first end that is configured to be coupled to a portion of tissue of a patient, the repair chord being configured to adjust a distance between the portion of tissue and the tissue-adjustment mechanism, in response to adjustment of the repair chord by the tissue-adjustment mechanism.

There is further provided, in accordance with an application of the present invention, a method, including:
coupling a guide member to a portion of tissue of a patient; and
advancing a tissue-adjustment mechanism toward the portion of tissue by:
threading a portion of the guide member through at least one channel extending between a first opening in an upper surface of the tissue-adjustment mechanism and a second opening in a lower surface of the tissue-adjustment mechanism; and
advancing the tissue-adjustment mechanism along the guide member and toward the portion of tissue.

There is further provided, in accordance with an application of the present invention, apparatus for use with tissue of a heart of a subject, the apparatus including:
at least one docking assembly, having:
a distal portion including a tissue anchor that is configured to engage a portion of the tissue,
a proximal portion, fixedly coupled to the distal portion, and including at least one docking station that includes a first coupling;
at least one guide member, reversibly coupled to the at least one docking station; and
an annuloplasty ring selected from the group consisting of: a partial annuloplasty ring and a full annuloplasty ring, the selected annuloplasty ring being:
shaped to define a second coupling, and
slidable along the guide member toward the docking station, and
configured to be locked to the docking station by the second coupling being lockable to the first coupling.

In an application, the second coupling is lockable to the first coupling by being pushed against the first coupling.

In an application, the annuloplasty ring is configured to be locked to the docking station suturelessly.

In an application, the docking assembly is percutaneously deliverable to the heart of the subject, and the annuloplasty ring is percutaneously lockable to the docking station.

In an application:
the at least one docking assembly includes a plurality of docking assemblies,
the at least one guide member includes a respective plurality of guide members, each of the guide members being reversibly coupled to a respective docking station of a respective docking assembly,
the selected annuloplasty ring is shaped to define a respective plurality of second couplings, and is slidable along the plurality of guide members toward the plurality of docking assemblies, and
the each of the second couplings is lockable to a respective first coupling of a respective docking assembly.

In an application, the selected annuloplasty ring includes an adjustable annuloplasty ring, including a rotatable structure that is:
bidirectionally rotatable to adjust the selected annuloplasty ring,
shaped to define a channel between an upper surface thereof and a lower surface thereof, the guide member being disposable in the channel, and
shaped to define the second coupling, and
the selected annuloplasty ring is slidable along the guide member by the rotatable structure being slidable along the guide member.

In an application:
the selected annuloplasty ring includes:
a sleeve, having a longitudinal length from a first end thereof to a second end thereof, and defining lumen therebetween,
a flexible longitudinal member, at least part of which is disposed in at least part of the lumen, and
the rotatable structure, and
the rotatable structure is:
coupled to a first end portion of the flexible longitudinal member, and
bidirectionally rotatable to adjust the longitudinal length of the sleeve by adjusting a degree of tension of the flexible longitudinal member.

In an application, the apparatus further includes a rotatable structure locking mechanism displaceable with respect to the rotatable structure, so as to release the rotatable structure during rotation of the rotatable structure, and lock in place the rotatable structure following rotation of the rotatable structure.

In an application, the apparatus further includes a release rod:
shaped to define a lumen therethrough, the guide member being disposable within the lumen of the release rod, and
configured to unlock the rotatable structure locking mechanism by being slid over the guide member.

There is further provided, in accordance with an application of the present invention, apparatus, including:
a docking assembly:
having a distal portion including a tissue anchor that is configured to engage cardiac tissue of a subject,
having a proximal portion including at least one docking station that includes a first coupling;
a guide member reversibly coupled to the at least one docking station; and
an adjustable annuloplasty ring selected from the group consisting of: a partial annuloplasty ring and a full annuloplasty ring, the selected annuloplasty ring:
a. including:
a sleeve, having a longitudinal length from a first end thereof to a second end thereof, and defining lumen therebetween,
a flexible longitudinal member, at least part of which is disposed in at least part of the lumen, and
a rotatable structure:
coupled to a first end portion of the flexible longitudinal member,
bidirectionally rotatable to adjust the longitudinal length of the sleeve by adjusting a degree of tension of the flexible longitudinal member,
shaped to define (1) a channel between an upper surface thereof and a lower surface thereof, the guide member being disposable in the channel, and (2) a second coupling, and
b. being slidable along the guide member toward the docking assembly, and configured to lock the selected annuloplasty ring to the docking assembly by the second coupling being lockable to the first coupling.

In an application, the apparatus further includes a rotatable structure locking mechanism displaceable with respect to the rotatable structure, so as to release the rotatable structure during rotation of the rotatable structure, and lock in place the rotatable structure following rotation of the rotatable structure.

In an application, the apparatus further includes a release rod:
shaped to define a lumen therethrough, the guide member being disposable within the lumen of the release rod, and
configured to unlock the rotatable structure locking mechanism by being slid over the guide member.

There is further provided, in accordance with an application of the present invention, a method for use with tissue of a heart of a subject, the method including:
advancing a docking station assembly to the tissue, the docking station assembly including (1) a distal portion including a tissue anchor that is configured to engage a portion of the tissue, and (2) a proximal portion, fixedly coupled to the distal portion, and including at least one docking station that includes a first coupling;
advancing, along a guide member that is reversibly coupled to the docking station, an annuloplasty ring selected from the group consisting of: a partial annuloplasty ring and a full annuloplasty ring, the selected annuloplasty ring being shaped to define a second coupling; and
locking the selected annuloplasty ring to the docking station by locking the second coupling to the first coupling.

There is further provided, in accordance with an application of the present invention, apparatus for use with at least one implant, including:
a tissue-engaging element having (a) a distal portion configured to engage at least a first portion of tissue of a patient, and (b) a proximal portion;
at least one docking station coupled to the proximal portion of the tissue-engaging element, the at least one docking station:
being configured to receive and be coupled to the at least one implant, and
including a locking mechanism configured to lock the implant to the docking station; and
at least one guide member reversibly coupled to the at least one docking station, the at least one guide member being configured for facilitating slidable advancement of the at least one implant toward the docking station.

In an application, the at least one docking station includes two or more docking stations, and the at least one guide member includes two or more guide members, each guide member being reversibly coupled to a respective docking station.

In an application, the implant includes at least one implant selected from the group consisting of: a prosthetic cardiac valve and a support for receiving a prosthetic cardiac valve, and the at least one docking station is configured to receive and be coupled to the selected implant.

In an application, the implant includes a tissue-adjustment device selected from the group consisting of: a partial annuloplasty ring and a full annuloplasty ring, and the at least one docking station is configured to receive and be coupled to the selected tissue-adjustment device.

In an application, the apparatus further includes the implant.

In an application, the implant has:
an upper surface and a lower surface,
at least one first opening at the upper surface,
at least one second opening at the lower surface, and
a channel extending between the first and second openings, the channel facilitating advancement of the implant along the guide member.

In an application, the implant includes a first coupling, and the locking mechanism includes a second coupling configured to be coupled to the first coupling.

In an application, the second coupling includes at least one depressed portion, and the first coupling includes at least one moveable baffle which is configured to engage the at least one depressed portion of the second coupling.

In an application, the apparatus further includes at least one flexible longitudinal member coupled at a first portion thereof to the implant, a second portion of the flexible longitudinal member is configured to be coupled to a second portion of tissue of the patient, and the implant is configured to adjust a length of the longitudinal member between the first and second portions of tissue.

In an application:
the first portion of tissue includes a first portion of cardiac tissue at a first intraventricular site,
the second portion of tissue includes at least one leaflet of an atrioventricular valve of the patient, and
the flexible longitudinal member includes at least one artificial chordea tendinea.

In an application:
the implant includes a rotatable structure,
the at least one flexible longitudinal member is coupled at the first portion to the rotatable structure, and
the rotatable structure is bidirectionally rotatable to adjust the degree of tension of the at least one flexible longitudinal member.

In an application, the rotatable structure is configured such that:
rotation of the rotatable structure in a first rotational direction applies tension to the flexible longitudinal member, and
rotation of the rotatable structure in a second rotational direction that is opposite the first rotational direction slackens the flexible longitudinal member.

In an application, the apparatus further includes a rotatable structure locking mechanism displaceable with respect to the rotatable structure, so as to:
release the rotatable structure during rotation of the rotatable structure, and lock in place the rotatable structure following rotation of the rotatable structure.

In an application, the rotatable structure includes a spool, and the at least one flexible longitudinal member is configured to be wound around the spool during the rotation of the spool in a first rotational direction.

In an application:
the implant includes a rotatable structure, coupled to a flexible longitudinal member,
the rotatable structure is bidirectionally rotatable to adjust a degree of tension of the flexible longitudinal member, and
the at least one docking station is configured to receive and be coupled to the rotatable structure.

There is further provided, in accordance with an application of the present invention, apparatus for use with at least one implant, including:
a tissue-engaging element having (a) a distal portion configured to engage at least a first portion of tissue of a patient, and (b) a proximal portion;
at least one docking station coupled to the proximal portion of the tissue-engaging element, the at least one docking station:
being configured to receive and be coupled to the at least one implant, and
including a locking mechanism configured to lock the implant to the tissue-engaging element; and
at least one guide member reversibly coupled to the at least one docking station, the at least one guide member being configured for facilitating slidable advancement of the at least one implant toward the tissue-engaging element.

In an application, the guide member is looped around a portion of the docking station.

In an application, the at least one docking station includes two or more docking stations, and the at least one guide member includes two or more guide members, each guide member being reversibly coupled to a respective docking station.

In an application, the implant includes a prosthetic cardiac valve.

In an application, the implant includes a support for receiving a prosthetic cardiac valve.

In an application, the implant includes a tissue-adjustment device.

In an application, the tissue-adjustment device includes an annuloplasty ring structure selected from the group consisting of: a partial annuloplasty ring and a full annuloplasty ring.

In an application, the apparatus further includes the implant, and the implant has:
an upper surface and a lower surface,
at least one first opening at the upper surface,
at least one second opening at the lower surface, and
a channel extending between the first and second opening, the channel facilitating advancement of the implant along the guide member.

In an application, the implant includes a prosthetic cardiac valve.

In an application, the implant includes a support for receiving a prosthetic cardiac valve.

In an application, the implant includes a tissue-adjustment device.

In an application, the tissue-adjustment device includes an annuloplasty ring structure selected from the group consisting of: a partial annuloplasty ring and a full annuloplasty ring.

In an application, the implant includes a first coupling, and the locking mechanism includes a second coupling configured to be coupled to the first coupling.

In an application, the second coupling includes at least one depressed portion, and the first coupling includes at least one moveable baffle which is configured to engage the at least one depressed portion of the second coupling.

In an application, the apparatus further includes at least one flexible longitudinal member coupled at a first portion thereof to the implant, a second portion of the flexible longitudinal member is configured to be coupled to a second portion of tissue of the patient, and the implant is configured to adjust a length of the longitudinal member between the first and second portions of tissue.

In an application:
the first portion of tissue includes a first portion of cardiac tissue at a first intraventricular site,
the second portion of tissue includes at least one leaflet of an atrioventricular valve of the patient, and
the flexible longitudinal member includes at least one artificial chordea tendinea.

In an application:
the implant includes a rotatable structure,
the at least one flexible longitudinal member is coupled at the first portion to the rotatable structure, and
the rotatable structure is bidirectionally rotatable to adjust the degree of tension of the at least one flexible longitudinal member.

In an application, during rotation of the rotatable structure in a first rotational direction, successive portions of the flexible longitudinal member advance in a first advancement direction with respect to the rotatable structure and contact the rotatable structure, to pull the second portion of the flexible member toward the rotatable structure, and to draw the first and second portions of tissue toward each other.

In an application, the apparatus further includes a rotatable structure locking mechanism displaceable with respect to the rotatable structure, so as to:

release the rotatable structure during rotation of the rotatable structure, and lock in place the rotatable structure following rotation of the rotatable structure.

In an application, the rotatable structure includes a spool, and the at least one flexible longitudinal member is configured to be wound around the spool during the rotation of the spool in a first rotational direction.

In an application, the first portion of the at least one flexible longitudinal member is looped through a portion of the spool.

In an application, the first portion of the at least one flexible longitudinal member is wound around a portion of the spool, and the first portion of the at least one flexible longitudinal member is configured to be unwound from around the portion of the spool following the coupling of the second portion of the flexible longitudinal member to the second portion of tissue of the patient.

There is further provided, in accordance with an application of the present invention, apparatus, including:

a tissue-engaging element having a distal portion configured to engage at least a first portion of tissue of a patient, and having a proximal portion;

at least one docking station coupled to the proximal portion of the tissue-engaging element, the at least one docking station being configured to be coupled to the at least one tissue-adjustment device;

an implant including:

a rotatable structure; and at least one flexible longitudinal member having a first portion thereof that is in contact with the rotatable structure, and a second portion thereof that is configured to be coupled to a second portion of tissue of the patient, and during rotation of the rotatable structure in a first rotational direction, successive portions of the flexible longitudinal member advance in a first advancement direction with respect to the rotatable structure and contact the rotatable structure, and, pull the second portion of the flexible longitudinal member toward the implant, and responsively, to draw the first and second portions of tissue toward each other; and at least one guide member reversibly coupled to the at least one docking station, the at least one guide member being configured for facilitating slidable advancement of the at least one implant toward the tissue-engaging element.

In an application, the guide member is looped around a portion of the docking station.

In an application, the at least one docking station includes two or more docking stations, and the at least one guide member includes two or more guide members, each guide member being reversibly coupled to a respective docking station.

In an application, the implant includes a support for receiving a prosthetic cardiac valve.

In an application, the implant includes a tissue-adjustment device.

In an application, the tissue-adjustment device includes an annuloplasty ring structure selected from the group consisting of: a partial annuloplasty ring and a full annuloplasty ring.

In an application, the implant has:

an upper surface and a lower surface, at least one first opening at the upper surface, at least one second opening at the lower surface, and a channel extending between the first and second opening, the channel facilitating advancement of the implant along the guide member.

In an application, the implant includes a first coupling, and the docking station includes a second coupling configured to be coupled to the first coupling.

In an application, the second coupling includes at least one depressed portion, and the first coupling includes at least one moveable baffle which is configured to engage the at least one depressed portion of the second coupling.

In an application, the second coupling includes a locking mechanism configured to lock the implant to the tissue-engaging element.

In an application:

the first portion of tissue includes a first portion of cardiac tissue at a first intraventricular site, the second portion of tissue includes at least one leaflet of an atrioventricular valve of the patient, and the flexible longitudinal member includes at least one artificial chordea tendinea.

In an application, the rotatable structure is rotatable in a first rotational direction to apply tension to the flexible longitudinal member, and in a second rotational direction that is opposite the first rotational direction to slacken the flexible longitudinal member.

In an application, during rotation of the rotatable structure in a first rotational direction thereof, successive portions of the flexible longitudinal member advance in a first advancement direction with respect to the rotatable structure and contact the rotatable structure, responsively, to pull the second portion of the flexible longitudinal member toward the rotatable structure.

In an application, the apparatus further includes a rotatable structure locking mechanism, displaceable with respect to the rotatable structure so as to:

release the rotatable structure during rotation of the rotatable structure, and lock in place the rotatable structure following rotation of the rotatable structure.

In an application, the rotatable structure includes a spool, and the at least one flexible longitudinal member is configured to be wound around the spool during the rotation of the spool in the first rotational direction.

In an application, the first portion of the flexible longitudinal member is looped through a portion of the spool.

In an application, the first portion of the flexible longitudinal member is wound around a portion of the spool, and the first portion of the flexible longitudinal member is configured to be unwound from around the portion of the spool following the coupling of the second portion of the flexible longitudinal member to the second portion of tissue of the patient.

There is further provided, in accordance with an application of the present invention, apparatus, including:

a guide member;

a tissue-adjustment mechanism having:

an upper surface and a lower surface, at least one first opening at the upper surface, at least one second opening at the lower surface, and a channel extending between the first and second openings, the channel facilitating advancement of the tissue-adjustment mechanism along the guide member; and at least one repair chord coupled at a first portion thereof to the tissue-adjustment mechanism and having at least a first end that is configured to be coupled to a portion of tissue of a patient, the repair chord being configured to adjust a distance between the portion of tissue and the tissue-adjustment mechanism, in response to adjustment of the repair chord by the tissue-adjustment mechanism.

The present invention will be more fully understood from the following detailed description of embodiments thereof, taken together with the drawings, in which:

DETAILED DESCRIPTION OF EMBODIMENTS

Figure 1:
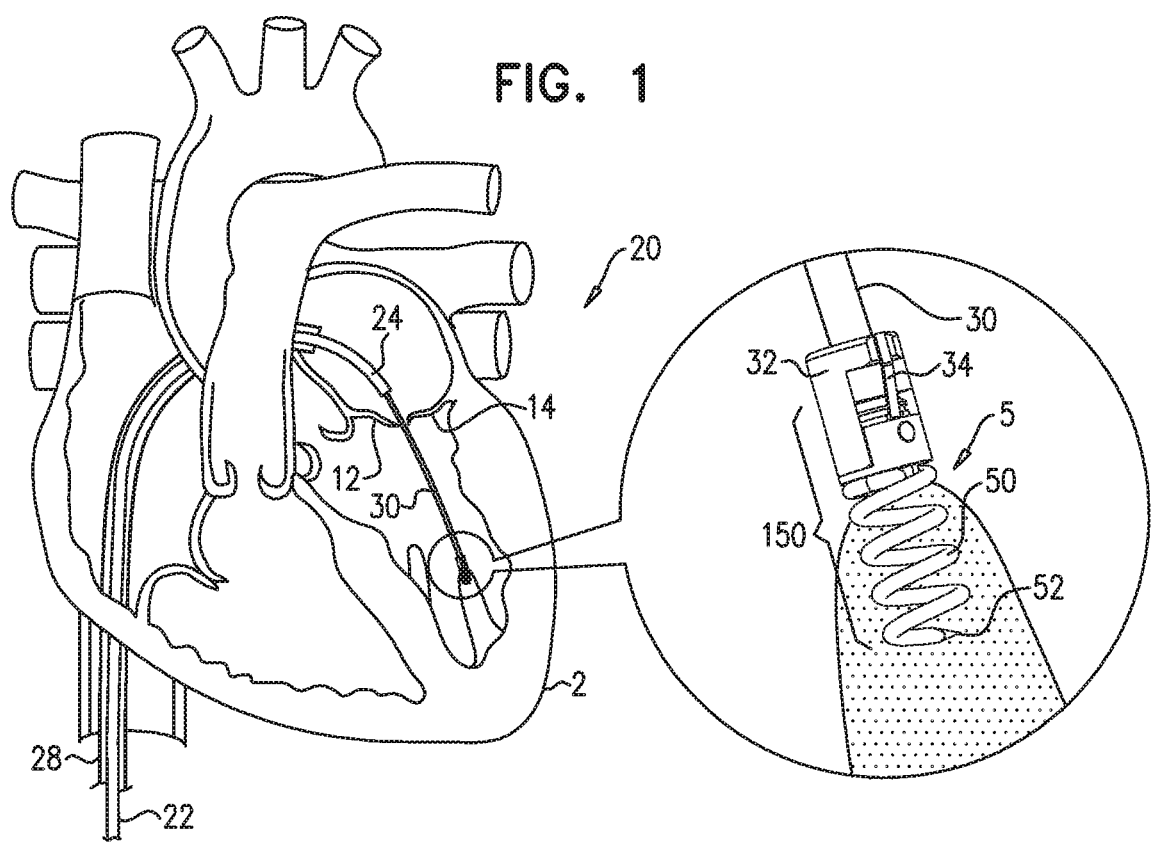
FIGS. 1-2 are schematic illustrations of apparatus comprising a tissue-engaging element comprising a docking station coupled to a guide wire, in accordance with some applications of the present invention.
Figure 2:
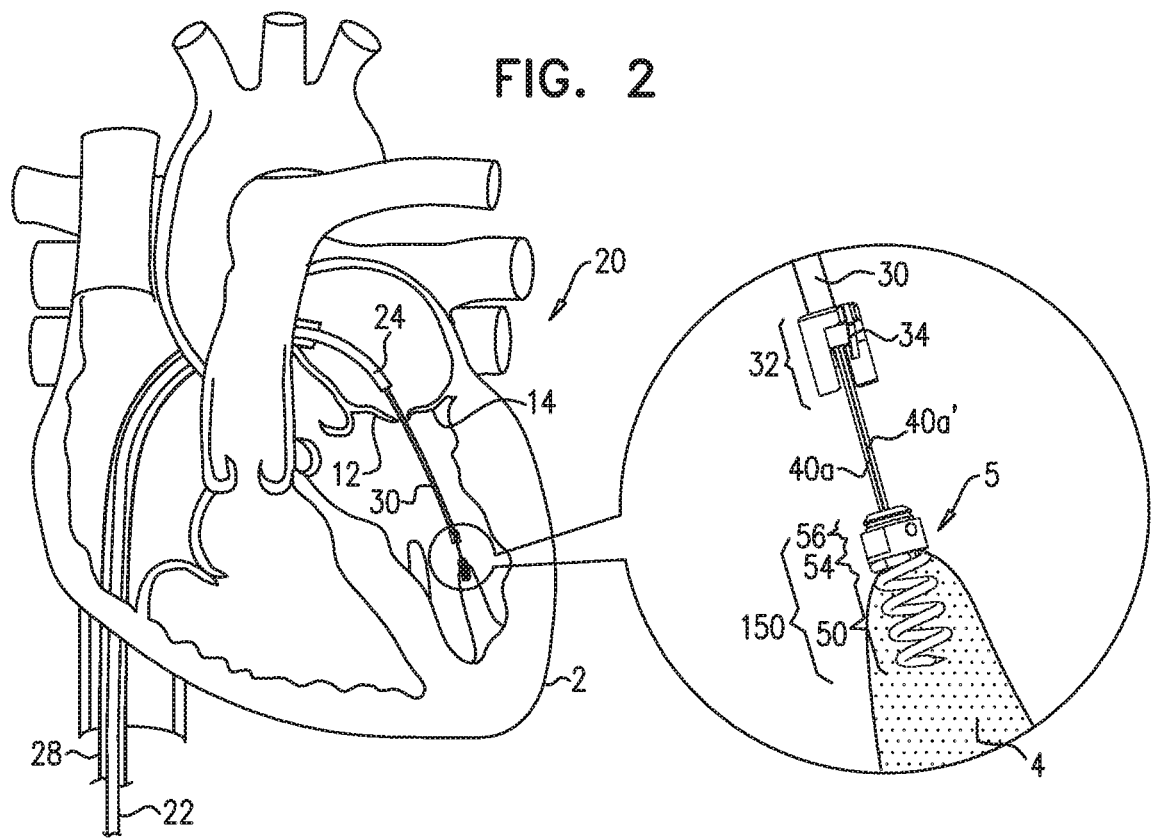

Reference is now made to FIGS. 1-2, which are schematic illustrations of a system 20 comprising a docking assembly 150 for implantation at a first implantation site 5 of a patient, in accordance with some applications of the present invention. As shown in FIG. 2, docking assembly 150 comprises a tissue-engaging element having (1) a distal portion comprising a tissue anchor 50 (e.g., a helical tissue anchor as shown by way of illustration and not limitation), and (2) a proximal portion comprising a docking platform 54, and at least one docking station 56. Thus, docking assembly 150 comprises (a) the distal portion which engages the tissue of the patient (i.e., the tissue-engaging element), and (b) the proximal portion which is coupled to docking station 56. It is to be noted that the distal portion and the proximal portion are fixedly coupled to each other (e.g., immovable with respect to each other), and thereby docking station 56 and tissue anchor 50 are fixedly coupled to each other (e.g., immovable with respect to each other). Docking assembly 150 is thereby an integrated unit that comprises the docking station and tissue anchor. At least one guide member, (e.g., a guide wire 40, shown in FIG. 2) is reversibly coupled to docking assembly 150 (e.g., by being looped around, or otherwise coupled to, a portion of assembly 150) so as to define first and second portions 40a and 40a' that extend away from assembly 150.

Tissue anchor 50 is typically implanted within cardiac tissue in a manner in which a distal portion of anchor 50 does not extend beyond an epicardium of heart 2 of the patient. Thus, anchor 50 is implanted at an intracardiac site such that the implant, (e.g., the adjustment mechanism or an implant comprising the adjustment mechanism) that is eventually coupled thereto (as described hereinbelow) is implanted at the intracardiac site such that no portions of the adjustment mechanism extend beyond the epicardium of the heart.

Docking assembly 150 and guide wire 40 are advanced toward implantation site typically during a transcatheter procedure, as shown. However, it is to be noted that the scope of the present invention includes the advancement of assembly 150 and guide wire 40 during a minimally-invasive or open-heart procedure. The procedure is typically performed with the aid of imaging, such as fluoroscopy, transesophageal echo, and/or echocardiography.

The transcatheter procedure typically begins with the advancing of a semi-rigid guide wire into a right atrium of the patient. The semi-rigid guide wire provides a guide for the subsequent advancement of a sheath 28 therealong and into the right atrium. Once sheath 28 has entered the right atrium, the semi-rigid guide wire is retracted from the patient's body. Sheath 28 typically comprises a 13-20 F sheath, although the size may be selected as appropriate for a given patient. Sheath 28 is advanced through vasculature into the right atrium using a suitable point of origin typically determined for a given patient. For example:

sheath 28 may be introduced into the femoral vein of the patient, through an inferior vena cava, into the right atrium, and into the left atrium transseptally, typically through the fossa ovalis;

sheath 28 may be introduced into the basilic vein, through the subclavian vein to the superior vena cava, into the right atrium, and into the left atrium transseptally, typically through the fossa ovalis; or sheath 28 may be introduced into the external jugular vein, through the subclavian vein to the superior vena cava, into the right atrium, and into the left atrium transseptally, typically through the fossa ovalis.

In some applications of the present invention, sheath 28 is advanced through the inferior vena cava of the patient (as shown) and into the right atrium using a suitable point of origin typically determined for a given patient.

Sheath 28 is advanced distally until the sheath reaches the interatrial septum. For some applications, a resilient needle and a dilator (not shown) are advanced through sheath 28 and into the heart. In order to advance sheath 28 trans septally into the left atrium, the dilator is advanced to the septum, and the needle is pushed from within the dilator and is allowed to puncture the septum to create an opening that facilitates passage of the dilator and subsequently sheath 28 therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 28 through the septum and into the left atrium is followed by the extraction of the dilator and the needle from within sheath 28. Subsequently, a docking-assembly delivery tool 30 is advanced through sheath 28. Tool 30 is typically advanced within a lumen of an advancement sheath 22 having a distal end 24. Advancement sheath 22 is advanced within sheath 28. Delivery tool 30 is coupled at a distal end thereof to a manipulator 32 which is reversibly coupled to docking station 56 and docking platform 54 of docking assembly 150. Manipulator 32 has (1) lateral arms which cup platform 54, and (2) a docking-station-coupler 34, as shown in FIG. 1. Coupler 34 is biased to move radially-inward, as shown in FIG. 1. Docking station 56 is ribbed, such that coupler 34, when moved radially inward, engages at least one rib of docking station 56, thereby coupling assembly 150 to delivery tool 30.

Delivery tool 30 and manipulator 32 are shaped so as to define a lumen for passage therethrough of guide wire 40.

Docking assembly 150 is implanted in implantation site 5 by rotating tool 30 in order to rotate anchor 50 and corkscrew anchor 50 into tissue of site 5. Site 5 typically comprises a portion of tissue at an intraventricular site in heart 2 of the patient. As shown, site 5 includes a papillary muscle 4, by way of illustration and not limitation. It is to be noted that site 5 includes any portion of cardiac tissue, e.g., a portion of a free wall of the ventricle, a portion of the septum facing the ventricle, a portion of tissue at a base of the papillary muscle, or a portion of the wall at the apex of the ventricle. (For the purposes of the claims, "a portion of tissue of a ventricle" includes any portion of cardiac tissue, e.g., a portion of a free wall of the ventricle, a portion of the septum facing the ventricle, a portion of tissue at a base of the papillary muscle, or a portion of the wall at the apex of the ventricle.)

Following the implantation of assembly 150 at site 5, tool 30 is disengaged from assembly 150 when the physician pulls on tool 30. This pulling pulls on manipulator 32 such that coupler 34 is actively moved radially outward against the ribs of docking station 56, and is thereby decoupled from station 56. At the time of pulling, tissue at implantation site 5 pulls on assembly 150 (in the direction opposite the direction of pulling by the physician) so as to help disengage tool 30 from assembly 150.

As shown in FIG. 2, following the decoupling of tool 30 from assembly 150, tool 30 is pulled proximally along guide wire 40 and is extracted from the body of the patient together with advancement sheath 22, leaving behind assembly 150 and guide wire 40.

Figure 3:
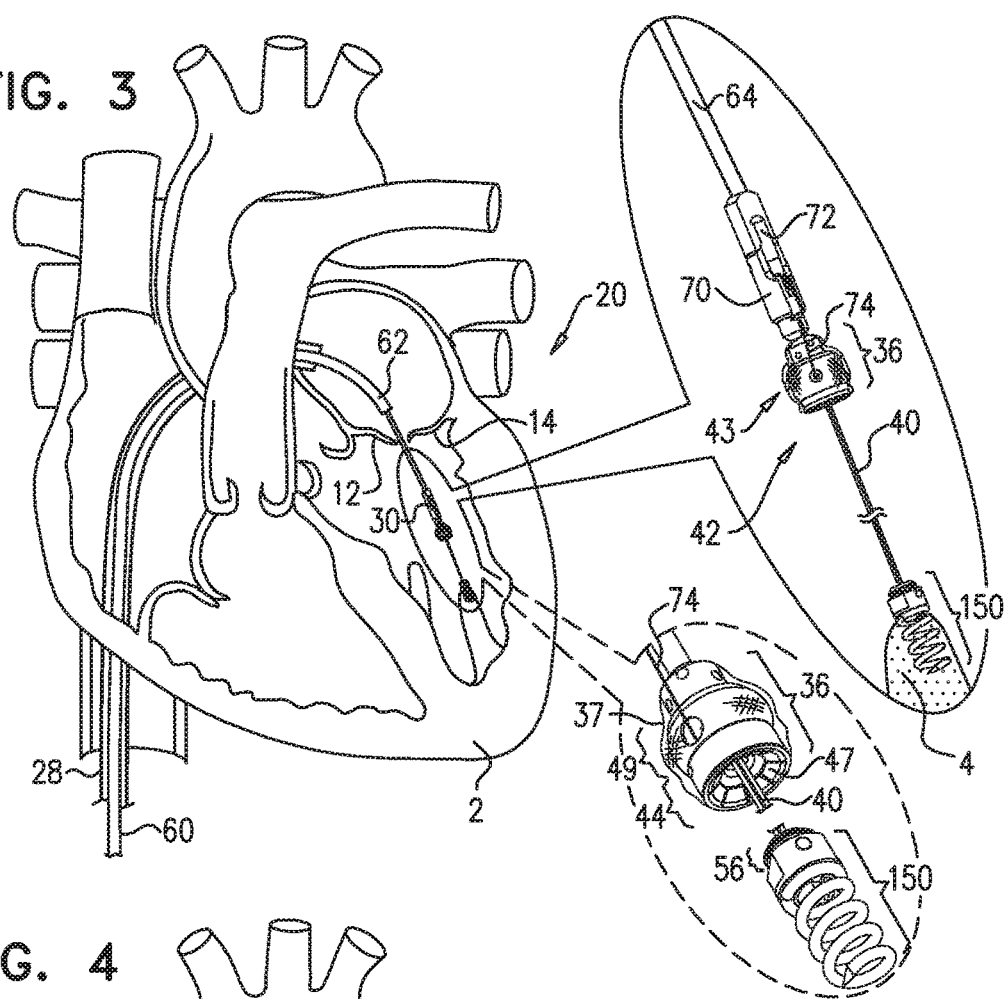
FIG. 3 is a schematic illustration of advancement of an adjustment mechanism along the guide wire toward the docking station of FIGS. 1 and 2, in accordance with some applications of the present invention.

FIG. 3 shows advancement of an implant (e.g., a spool assembly 36 comprising an adjustment mechanism 43) along guide wire 40 by an adjustment-mechanism delivery tool 64, in accordance with some applications of the present invention. Tool 64 is surrounded by and slidable within an advancement sheath 60 having a distal end 62.

Spool assembly 36 is surrounded by a braided fabric mesh, e.g., a polyester mesh, which promotes fibrosis around assembly 36 and facilitates coupling of assembly 36 to tissue of heart 2. Assembly 36 houses a rotatable structure (e.g., a spool as shown hereinbelow) that is surrounded by a housing 49. Housing 49 is coupled to a distal cap 44 which facilitates coupling of assembly 36 to docking station 56 of docking assembly 150. As shown, cap 44 is shaped so as to define a plurality of baffles 47 that are disposed angularly with respect to a distal end of cap 44. Baffles 47 are coupled to the distal end of cap 44 along respective coupling joints which facilitate movement of each baffle 47. During the coupling of spool assembly 36 to docking station 56, the ribbed portion of docking station 56 pushes inwardly baffles 47 of cap 44, as is described hereinbelow. Baffles 47 then expand and engage an area of docking station 56 between the ribs of the ribbed portion so as to dock and lock assembly 36 to docking station 56.

Additionally, cap 44 is shaped so as to define a central opening therethrough which facilitates passage therethrough of guide wire 40. Additionally, spool assembly 36 and the components thereof are shaped so as to define a central opening (i.e., an opening having the same axis as guide wire 40). That is, spool 46 has a central opening, and housing 49 has a central opening which facilitates passage of spool 46 and housing 49 along guide wire 40.

As shown, adjustment mechanism 43 is coupled to a distal portion of a repair chord 74 (e.g., repair chord 74 is looped through or otherwise coupled to a portion of adjustment mechanism 43). Chord 74 comprises a flexible longitudinal member. For some applications, and as is described hereinbelow, chord 74 functions as an artificial chordea tendinea. A proximal portion of chord 74 is coupled to a leaflet-engaging element 72 (e.g., a clip, as shown). Leaflet-engaging element 72 is disposed within a holder 70 that is coupled to delivery tool 64. Chord 74 a superelastic, biocompatible material (e.g., nitinol, ePTFE, PTFE, polyester, stainless steel, or cobalt chrome). Typically, chord 74 comprises an artificial chordea tendinea.

Figure 4:
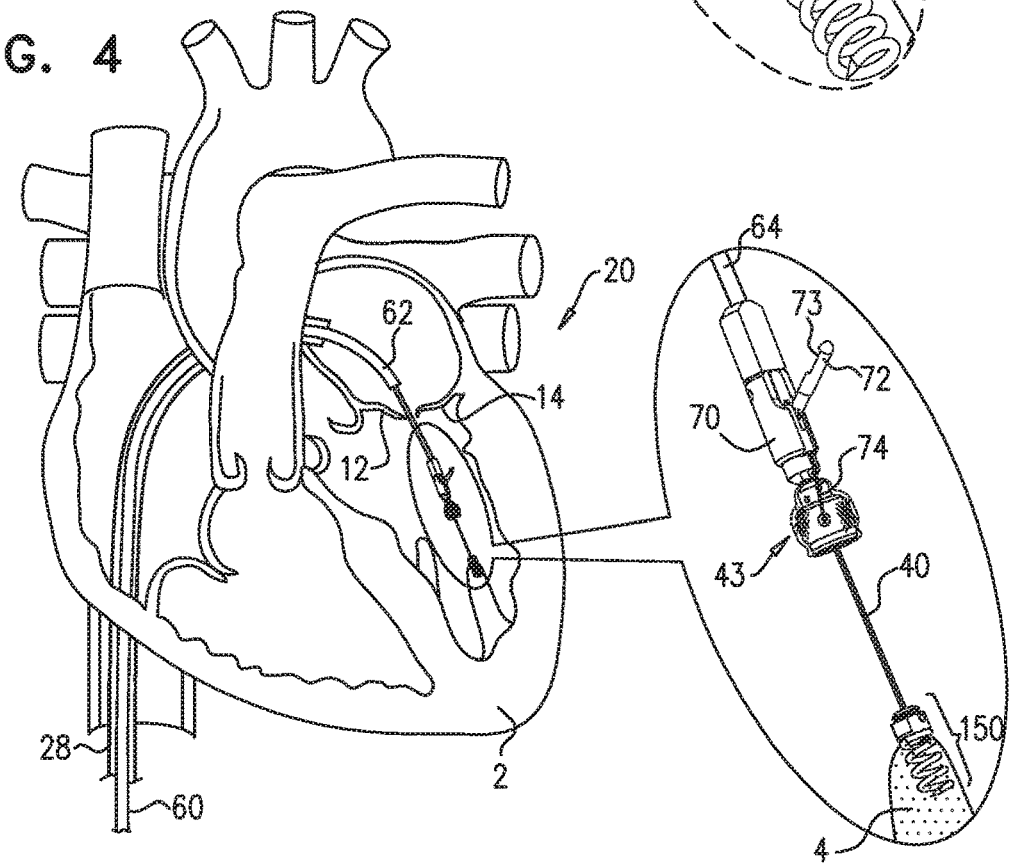
FIGS. 4-5 are schematic illustrations of engaging a leaflet with a leaflet engaging element, in accordance with some applications of the present invention.
Figure 5:
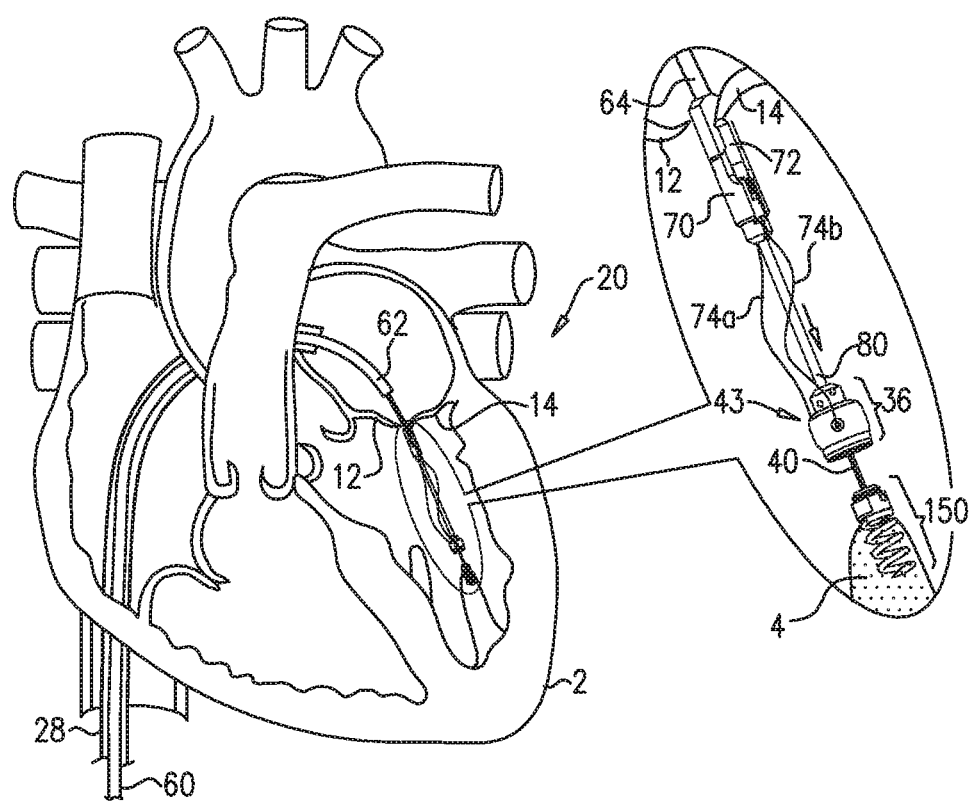

FIGS. 4-5 are schematic illustrations of the engaging of leaflet-engaging element 72 to at least one leaflet 14 of a mitral valve of the patient, in accordance with some applications of the present invention. As shown in FIG. 4, the clip is opened from a remote location outside the body of the patient.

For some applications, the clip typically is shaped so as to define at least one coupling protrusion 73. The clip has a tendency to close, and is initially held open by a cord (not shown) that is coupled to a surface of the clip, extends through delivery tool 64, and is held taught outside of the heart. Once the clip has been advanced to the desired location on the leaflet, the cord is relaxed, allowing the clip to close. The cord is removed, typically by releasing one end thereof and pulling the other end. The positioning of holder 70 between the leaflets (FIG. 5) helps ensure that the clip engages exactly one of the leaflets. It is noted that in FIG. 5 the clip is shown engaging only a single leaflet (leaflet 14). The clip typically engages the leaflet by clamping the leaflet such that the clip engages atrial and ventricular surfaces of the leaflet. The clip may puncture the leaflet, or may merely press firmly against the leaflet.

It is to be noted that the scope of the present invention includes the clipping together of both leaflets 12 and 14. For applications in which system 20 is used to repair a tricuspid valve of the patient, the clip may clip any one, two, or all three leaflets together.

Holder 70 is shaped to define a groove which houses the clip during the advancement of tool 64 toward the ventricle. The groove functions as a track to facilitate slidable detachment of the clip from holder 70 following the engaging of the clip to leaflet 14.

Alternatively, the clip has a tendency to open. In order to close the clip, a cord is provided. A distal-most portion of the cord is looped around the clip. Once the clip has been advanced to the desired location on the leaflet, as shown in FIG. 5, the surgeon pulls on both ends of the cord, thereby causing the clip to become locked closed. The cord is removed, typically by releasing one end thereof and pulling the other end.

It is to be noted that the scope of the present invention includes any leaflet-engaging element known in the art.

As shown in FIG. 5, portions 74a and 74b extend from leaflet-engaging element 72 toward adjustment mechanism 43. Portions 74a and 74b define portions of a single chord 74 that is looped through a portion of mechanism 43. Alternatively, portions 74a and 74b represent two distinct chords which are coupled at their distal ends to adjustment mechanism 43 and at their proximal ends to leaflet-engaging element 72.

As shown, leaflet-engaging element 72 engages leaflet 14 prior to coupling spool assembly 36 to docking station 56.

Figure 6:
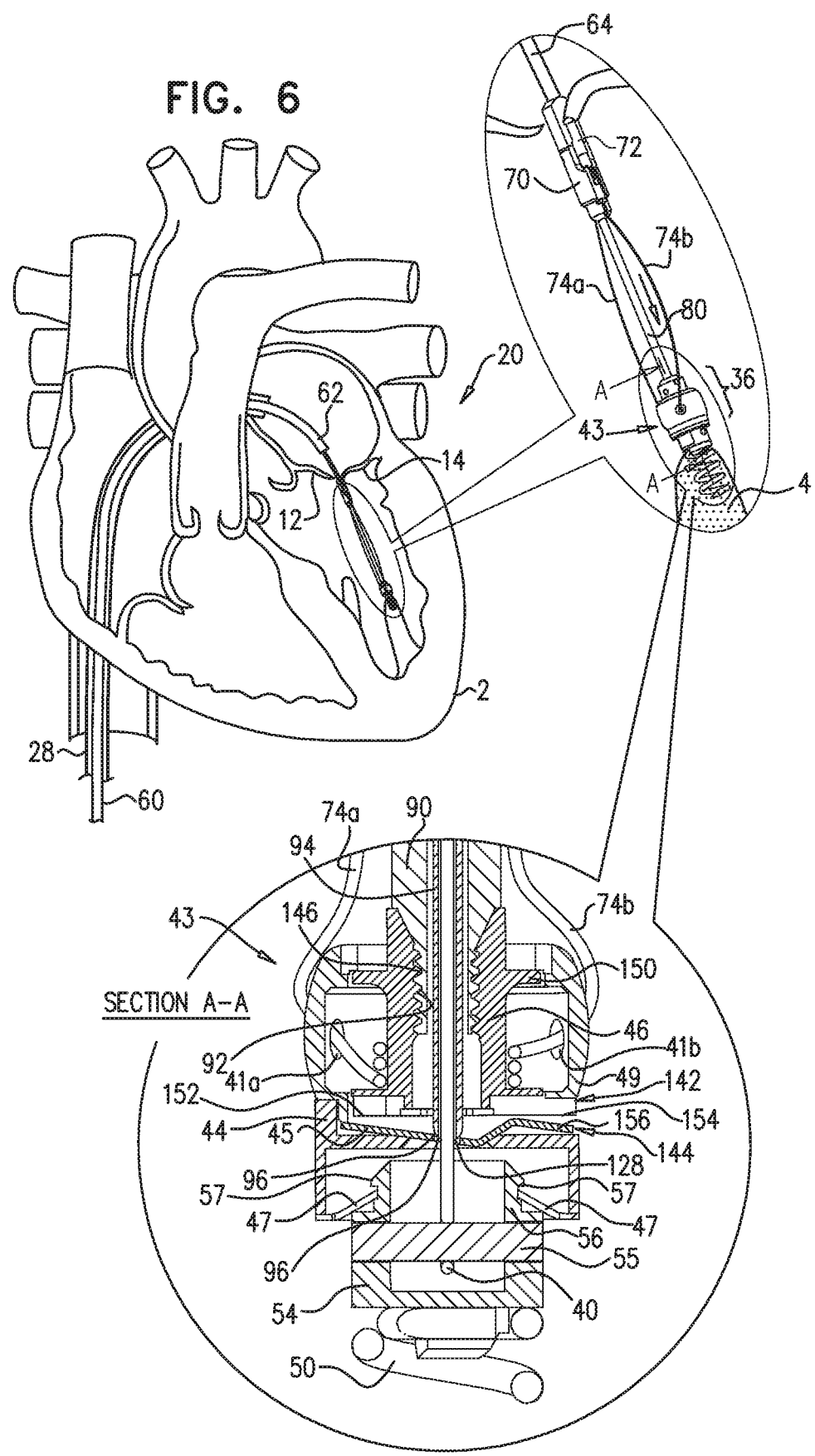
FIG. 6 is a schematic illustration of coupling of the adjustment mechanism of FIG. 3 to the docking station, in accordance with some applications of the present invention.

FIG. 6 shows spool assembly 36 being coupled to docking station 56, in accordance with some applications of the present invention. Following the coupling of leaflet-engaging element 72 to leaflet 14, spool assembly 36 is pushed distally toward docking station 56. Spool assembly 36 is coupled to an advancement shaft 80 which pushes assembly 36. Shaft 80 slides within a lumen of delivery tool 64 and within a lumen of holder 70 so as to advance spool assembly 36, while leaflet-engaging element 72 remains engaged with leaflet 14. Advancement shaft 80 functions to advance distally spool assembly 36 and functions to facilitate engagement between spool assembly 36 and docking station 56.

As described hereinabove, docking station 56 has one or more locking mechanisms (e.g., one or more ribs 57, shown in the enlarged cross-sectional image of FIG. 6) which project laterally such that rib 57 defines a shelf and a depressed area underneath the shelf (i.e., the cross-sectional diameter at rib 57 is larger than the cross-sectional diameter at the area underneath the shelf). As described hereinabove, cap 44 of assembly 36 is shaped so as to define a plurality of baffles 47. As cap 44 engages docking station 56, baffles 47 are pushed inward and upward angularly as each baffle slides against rib 57. After each baffle 47 passes the shelf of rib 57, the baffle engages the depressed area underneath the shelf of rib 57, as shown in the enlarged cross-sectional image of FIG. 6. The shelf of rib 57 prevents upward movement of baffles 47 and thereby locks in place baffles 47 and cap 44 with respect to docking station 56. Rib 57, therefore, comprises a locking mechanism so as to lock implant 42 (e.g., adjustment mechanism 43) to tissue anchor 50.

Following the coupling of assembly 36 to docking station 56, spool 46 is rotated in a first rotational direction in order to advance with respect to spool 46 and contact with spool 46 successive portions of chord 74. For example, when the successive portions of chord 74 are advanced with respect to spool 46, the successive portions of chord 74 are looped around spool 46. The rotating of spool 46 in the first rotational direction pulls tight and adjusts a length of chord 74 between leaflet 14 and spool 46, in order to adjust a distance between leaflet 14 and implantation site 5 and to facilitate coaptation between leaflets 12 and 14, as is described hereinbelow.

Housing 49 is shaped so as to provide openings 41a and 41b for passage therethrough of portions 74a and 74b, respectively, of chord 74 into housing 49. For some applications of the present invention, portions 74a and 74b define portions of a single chord 74 that is looped through spool 46. For other applications, portions 74a and 74b define discrete chords which are each coupled at respective distal ends thereof to spool 46.

The enlarged, cross-sectional image of FIG. 6 shows spool 46 within housing 49. Spool 46 defines an upper surface 150, a lower surface 152, and a cylindrical body portion disposed vertically between surfaces 150 and 152. Spool 46 is shaped to provide a driving interface, e.g., a channel, which extends from an opening provided by upper surface 150 to an opening provided by lower surface 152. A proximal portion of the driving interface is shaped to define a threaded portion 146 which may or may not be tapered. Threaded portion 146 of spool 46 is engageable by a threaded portion of a screwdriver head 92 of a screwdriver 90. Screwdriver 90 is coupled to a distal end of shaft 80. For some applications, shaft 80 rotates screwdriver 90. For other applications, shaft 80 is shaped so as to define a lumen for advancement therethrough of a screwdriver-rotation tool that facilitates rotation of screwdriver 90. Rotation of screwdriver 90 and screwdriver head 92 rotates spool 46, as the respective threaded portions of spool 46 and screwdriver head 92 engage. The cylindrical body portion of spool 46 is shaped to define one or more holes which function as respective coupling sites for coupling (e.g., looping through the one or more holes, or welding to spool 46 in the vicinity of the one or more holes) of any number of chords 74 to spool 46.

Lower surface 152 of spool 46 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially or otherwise, with respect to lower surface 152 of spool 46.

As shown, a locking mechanism 45 is disposed in communication with lower surface 152 of spool 46 and disposed in communication with at least in part to a lower surface of housing 49. Typically, a cap 44 maintains locking mechanism 45 in place with respect to lower surface 152 of spool 46 and lower surface of housing 49. For some applications, locking mechanism 45 is coupled, e.g., welded, to the lower surface of housing 49. Typically, locking mechanism 45 defines a mechanical element having a planar surface that defines slits. It is to be noted that the surface of locking mechanism 45 may also be curved, and not planar. Locking mechanism 45 is shaped to provide a protrusion 156 which projects out of a plane defined by the planar surface of the mechanical element. The slits of mechanism 45 define a depressible portion 128 that is disposed in communication with and extends toward protrusion 156. Depressible portion 128 is moveable in response to a force applied thereto typically by an elongate locking mechanism release rod 94 which slides through a lumen of screwdriver 90 and a torque-delivering tool that is coupled thereto.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

Cap 44 is provided that is shaped to define a planar surface and an annular wall having an upper surface thereof. The upper surface of the annular wall is coupled to, e.g., welded to, a lower surface provided by housing 49. The annular wall of cap 44 is shaped to define a recessed portion 144 of cap 44 that is in alignment with a recessed portion 142 of spool housing 49.

As shown, a distal end 96 of locking mechanism release rod 94 pushes distally on depressible portion 128 in order to unlock locking mechanism 45 from spool 46. Pushing depressible portion 128 by locking mechanism release rod 94 pushes distally protrusion 156 within recessed portion 142 of housing 49 and within recessed portion 144 of cap 44, which frees protrusion 156 from recesses 154 of spool 46. Once protrusion 156 is released from recesses 154 of spool 46, the physician is able to rotate spool 46 bidirectionally in order to adjust a tension of chord 74.

When the physician rotates spool 46 in the first rotational direction, chord 74 is pulled tight, and leaflet 14 is drawn toward adjustment mechanism 43 and toward anterior leaflet 12 of mitral valve 8.

In the resting state (i.e., prior to the rotation of spool 46 in order to adjust chord 74, following coupling of leaflet-engaging element 72 to leaflet 14) chord 74 is wrapped around spool 46 a few times (e.g., three times, by way of illustration and not limitation). This winding provides excess slack to chord 74 (in case portions 74a and 74b are coupled too tightly to leaflet 14). If the physician wishes to provide slack to member 74 or to any one of portion 74a or 74b, the physician unwinds a bit of the wrapped portion of member 74 from around spool 46 (e.g., by unwinding chord 74 a few times from around spool 46, or by unwinding chord 74 entirely from around spool 46 so that chord 74 slides freely through spool 46 within a channel provided therein). In order to accomplish such unwinding, the physician rotates spool 46 in a rotational direction in which it unwinds the wrapped portion of chord 74. Since chord 74 is looped through spool 46 in the channel provided therein, when chord 74 is unwound from spool 46, the physician can pull on one or both portions 74a and 74b so as to adjust, make even, or further slacken any one of or both portions 74a and 74b that extend from spool 46.

When the physician desires to pull tight chord 74, he or she effects rotation of spool 46 in a first rotational direction, i.e., the direction opposite the second rotational direction in which spool 46 is rotated during the unwinding of chord 74 from spool 46. Rotation of spool 46 in the first rotational direction winds chord 74 around spool 46, while rotation of spool 46 in a second rotational direction that is opposite the first rotational direction, unwinds the portion of longitudinal chord 74 from around spool 46.

Figure 7:
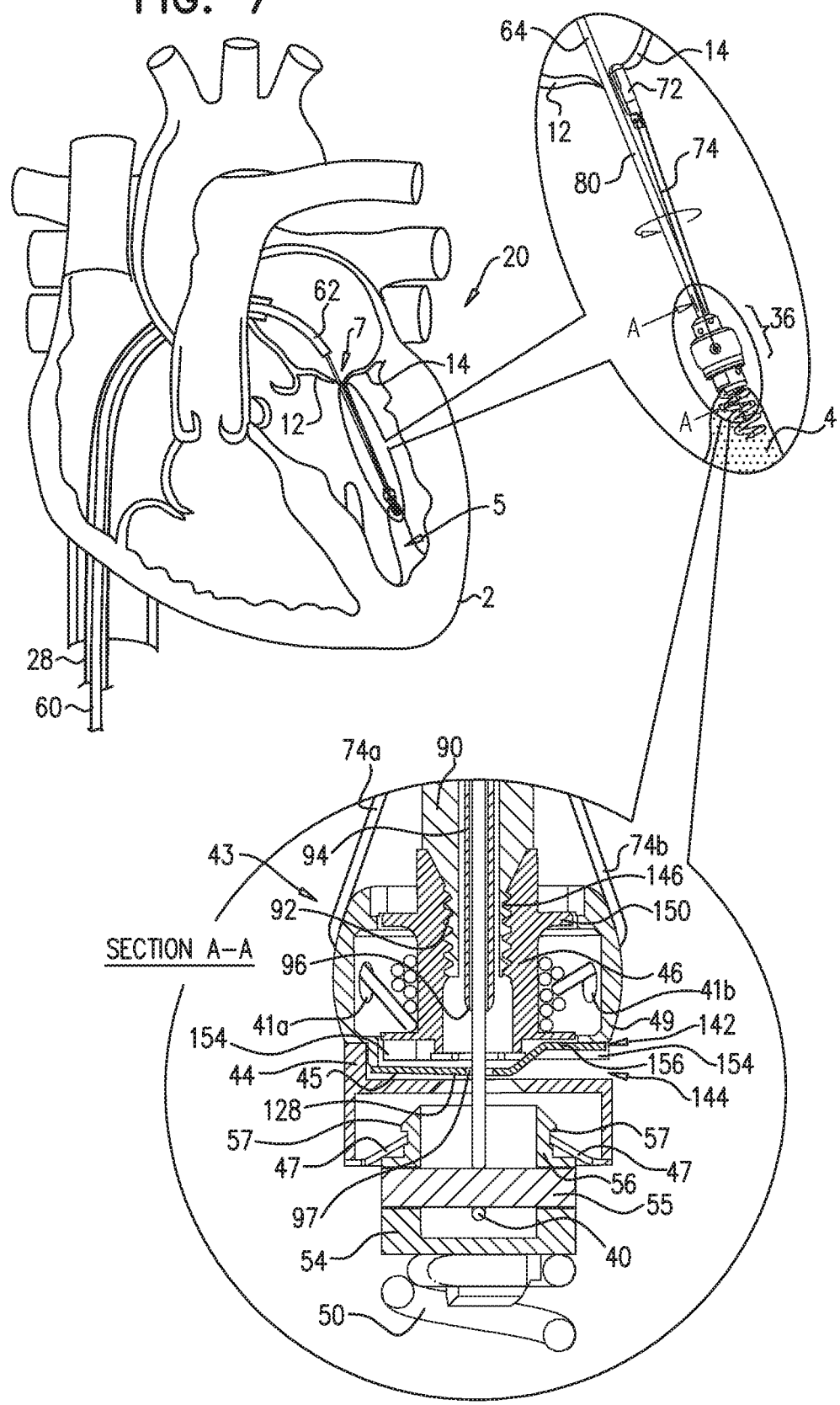
FIGS. 7-9 are schematic illustrations of adjusting by the adjustment mechanism a length of a repair chord coupled to the adjustment mechanism, in accordance with some applications of the present invention.

FIG. 7 shows spool assembly 36 following the adjustment of chord 74 by rotating screwdriver 90 in the direction as indicated by the arrow, and the partial removal of screwdriver 90, in accordance with some applications of the present invention. As shown in the enlarged cross-sectional image of FIG. 7, successive portions of chord 74 are wrapped around spool 46. That is, chord 74 is wrapped more times around spool 46 following adjustment (e.g., an additional 4 times, as shown in FIG. 7), than prior to adjustment (FIG. 6). This pulls chord 74 from a slackened state (FIG. 6) to a taut state (FIG. 7) in order to adjust a length of chord 74 between adjustment mechanism 43 and the proximal end of chord 74 that is coupled to leaflet-engaging element 72. Additionally, this applying of tension to chord 74 adjusts a length between first and second implantation sites 5 and 7. Typically, chord 74 is adjusted while heart 2 is beating.

As shown, rod 94 is shaped so as to define a central lumen and a distal opening for passage therethrough of guide wire 40. Additionally, depressible portion 128 is shaped so as to provide an opening for passage of guide wire 40 therethrough. Guide wire 40 is looped around a distal looping element 55 of docking platform 54 of docking assembly 150. Following the adjusting of the tension and length of chord 74, screwdriver 90 is decoupled from spool 46 (e.g., by being unscrewed from threaded portion 146 of spool 46) and is advanced proximally together with rod 94 away from spool assembly 36, as shown in the enlarged, cross-sectional image of FIG. 7.

Following the decoupling of screwdriver 90 from spool 46 and the removal of screwdriver 90, guide wire 40 remains coupled to docking platform 54 and docking assembly 150. Guide wire 40 then facilitates subsequent advancement of screwdriver 90 or any other tool to access spool assembly 36 and/or to facilitate further adjustment of chord 74 beyond the initial adjustment. Guide wire 40 may remain chronically coupled to docking assembly 150 and may be accessible at a subcutaneous location of the patient, e.g., a port. For other applications, guide wire 40 is removed from docking assembly 150 when the physician determines that further adjustment of chord 74 is not needed. The physician removes guide wire 40 by pulling, from outside the body of the patient, one end of guide wire 40 so that guide wire 40 slides around element 55 and is unlooped therefrom. The physician continues to pull on the end of guide wire 40 until the second end of wire 40 is exposed and removed from the patient.

Following the removal of locking-mechanism release rod 94, depressible portion 128 is no longer depressed by distal end 96 of rod 94, and protrusion 156 returns within a recess 154 of spool 46 so as to lock spool 46 in place and restriction rotation thereof in either direction (FIG. 7).

Reference is now made to FIGS. 3-7. It is to be noted that spool assembly 36 is only coupled to docking assembly 150 following the coupling of leaflet-engaging element 72 to leaflet 14. This is done in order to reduce the strain on implantation site 5. Should spool assembly 36 be implanted at implantation site 5 prior to engaging leaflet 14 with leaflet-engaging element 72, more strain would be applied to implantation site 5 than if spool assembly 36 had been implanted following the coupling of leaflet-engaging element 72 to leaflet 14, as described herein. That is, the pulling force is applied in a downward direction from leaflet 14 toward implantation site 5 instead of from implantation site 5 upward toward leaflet 14.

Figure 8:
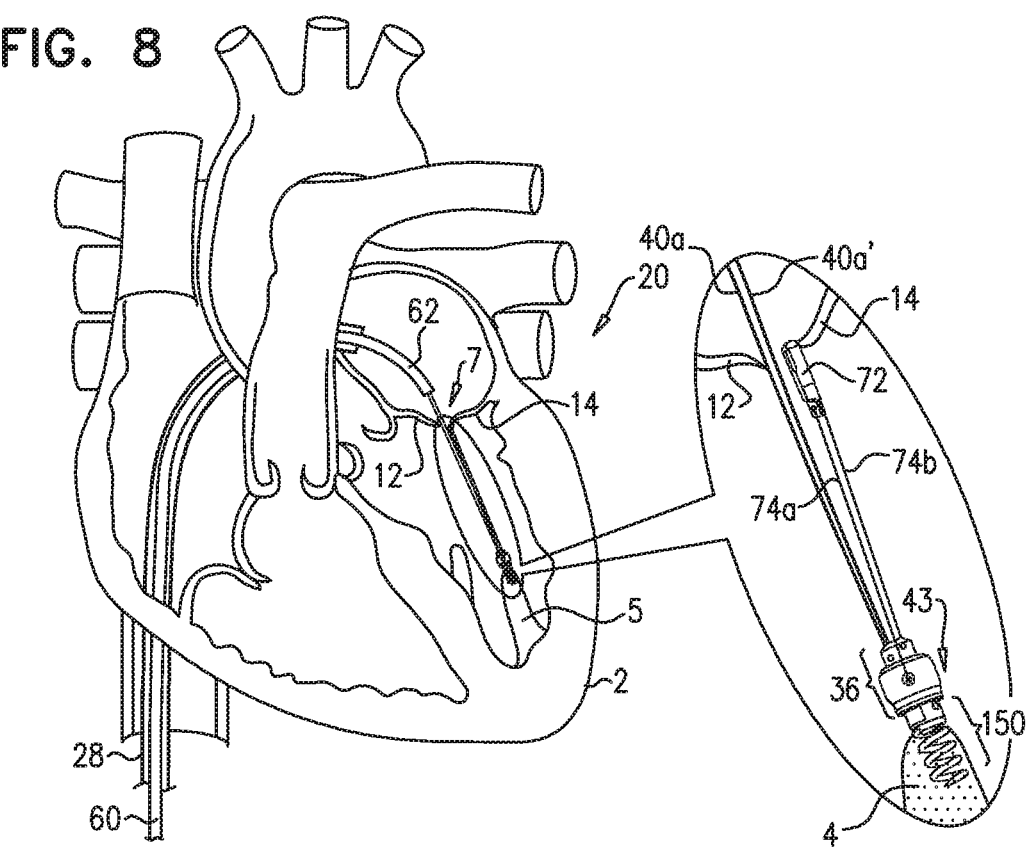

FIG. 8 shows system 20 following the removal of the tool used to rotate spool 46 of spool assembly 36, in accordance with some applications of the present invention. As shown, chord 74 is pulled tight such that its length and tension are adjusted, and leaflet 14 is pulled and adjusted commensurate with the adjustment of chord 74. Guide wire 40 remains coupled to spool assembly 36 and to docking assembly 150, as shown, such that portions 40a and 40a' extend from spool assembly 36. Guide wire 40 facilitates the reintroduction of the tool used to rotate spool 46, or of any other tool.

Figure 9:
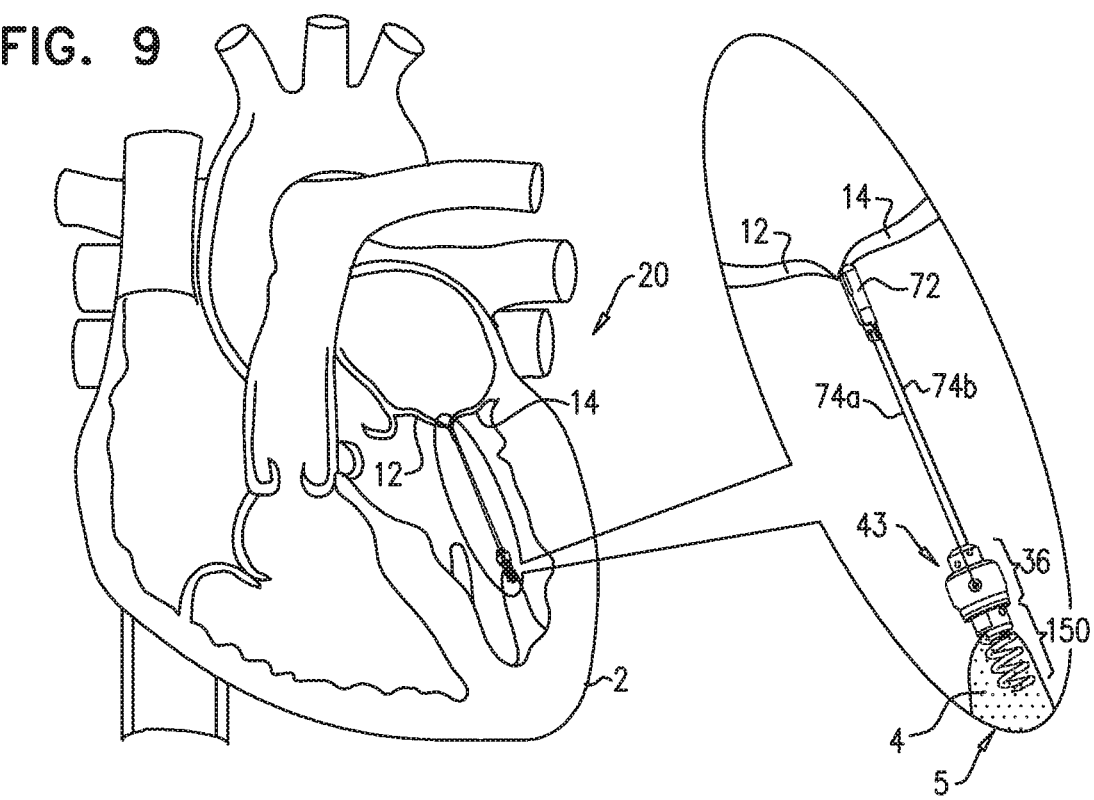

FIG. 9 shows system 20 following the removal of guide wire 40 from heart 2, in accordance with some applications of the present invention. As shown, the adjustment of chord 74 draws leaflets 12 and 14 together. It is to be noted that although leaflet-engaging element 72 is shown as engaging only leaflet 14, the scope of the present invention includes the engaging of both leaflets 12 and 14 by leaflet-engaging element 72.

Figure 10:
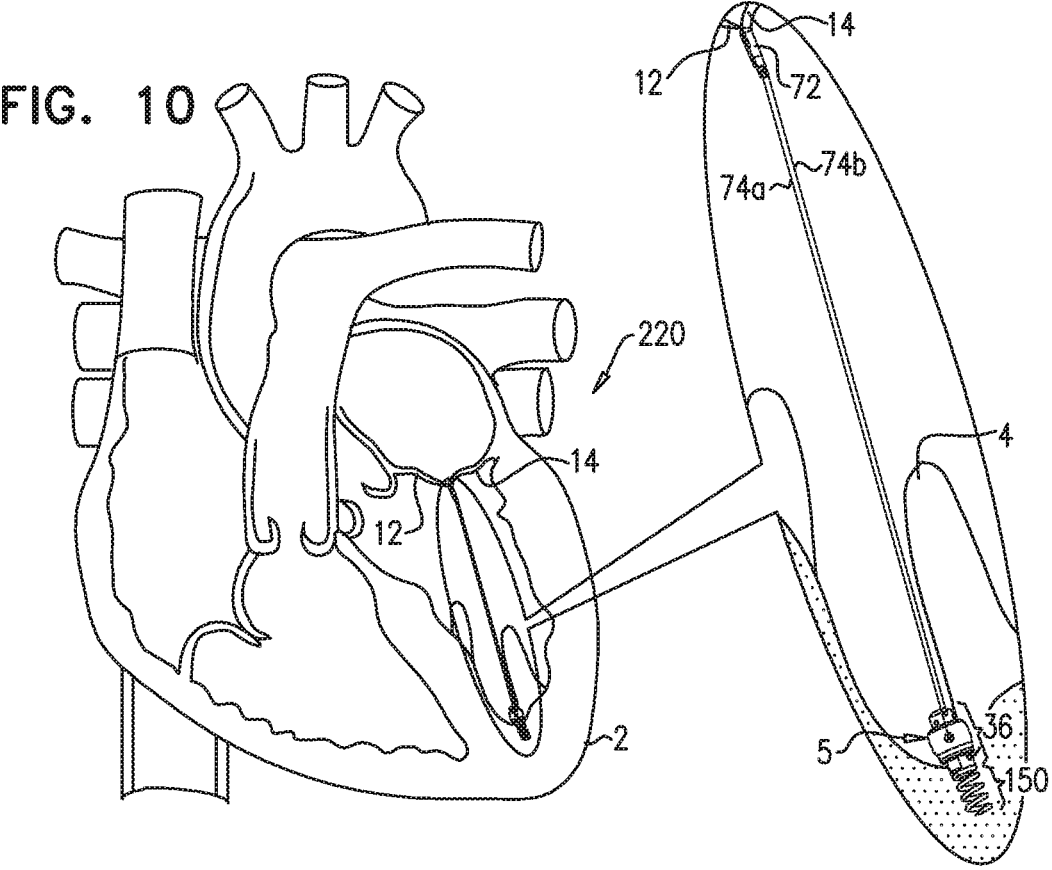
FIG. 10 is a schematic illustration of the adjustment mechanism and the repair chord, in accordance with some other applications of the present invention.

FIG. 10 shows a system 220, as described hereinabove with reference to system 20, with the exception that implantation site 5 includes tissue of the wall of the ventricle at the base of papillary muscle 4 in a vicinity of the apex of the heart, in accordance with some applications of the present invention. Implantation site 5 is shown by way of illustration and not limitation, and as described hereinabove, site 5 may include any portion of tissue of heart 2. It is to be noted that although leaflet-engaging element 72 is shown as engaging only leaflet 14, the scope of the present invention includes the engaging of both leaflets 12 and 14 by leaflet-engaging element 72.

FIGS. 11-15 are schematic illustrations of a system 320 comprising a multiple-docking-station assembly 350 comprising a plurality of docking stations 56, in accordance with some applications of the present invention. Multiple-docking-station assembly 350 comprises a tissue anchor 50 and a docking platform 322 which supports two or more docking stations 56. Platform 322, as shown, supports three docking stations 56a, 56b, and 56c, by way of illustration and not limitation. It is to be noted that platform 322 may support any number of docking stations 56. As shown, each docking station 56a, 56b, and 56c is reversibly coupled to a respective guide wire 40a, 40b, and 40c, in a manner as described hereinabove. Each docking station 56a, 56b, and 56c facilitates coupling thereto of a respective spool assembly 36a, 36b, and 36c, or any other tool or device which may be coupled to docking stations 56a, 56b, and 56c.

Figure 11:
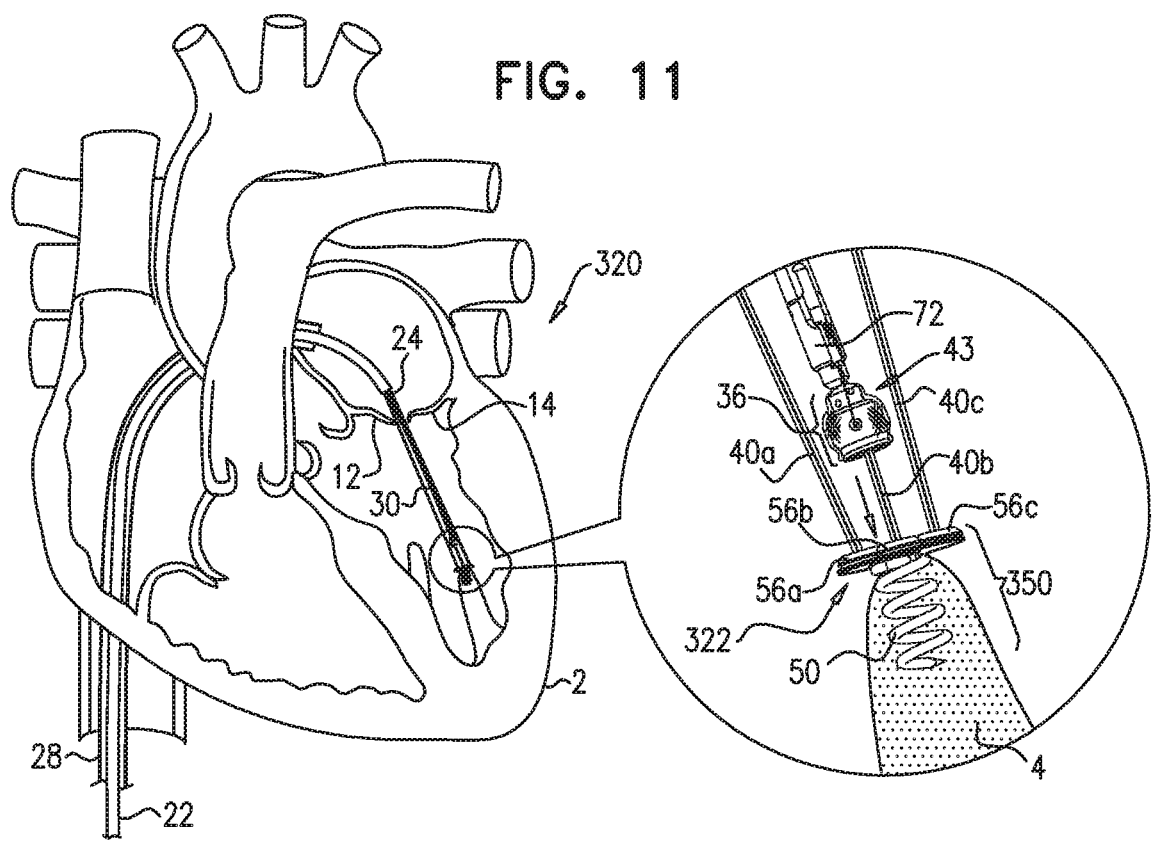
FIGS. 11-15 are schematic illustrations of a plurality of docking stations and a plurality of adjustment mechanisms, in accordance with some applications of the present invention.
Figure 12:
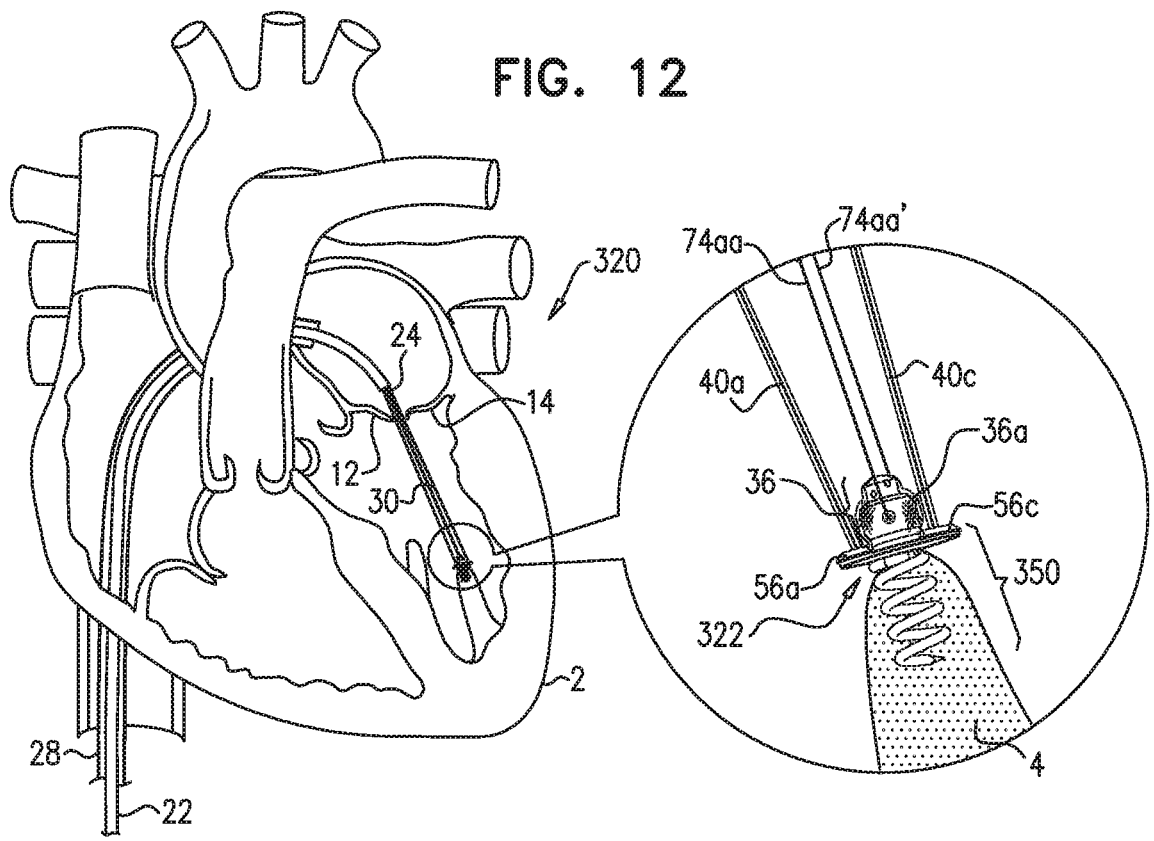
Figure 13:
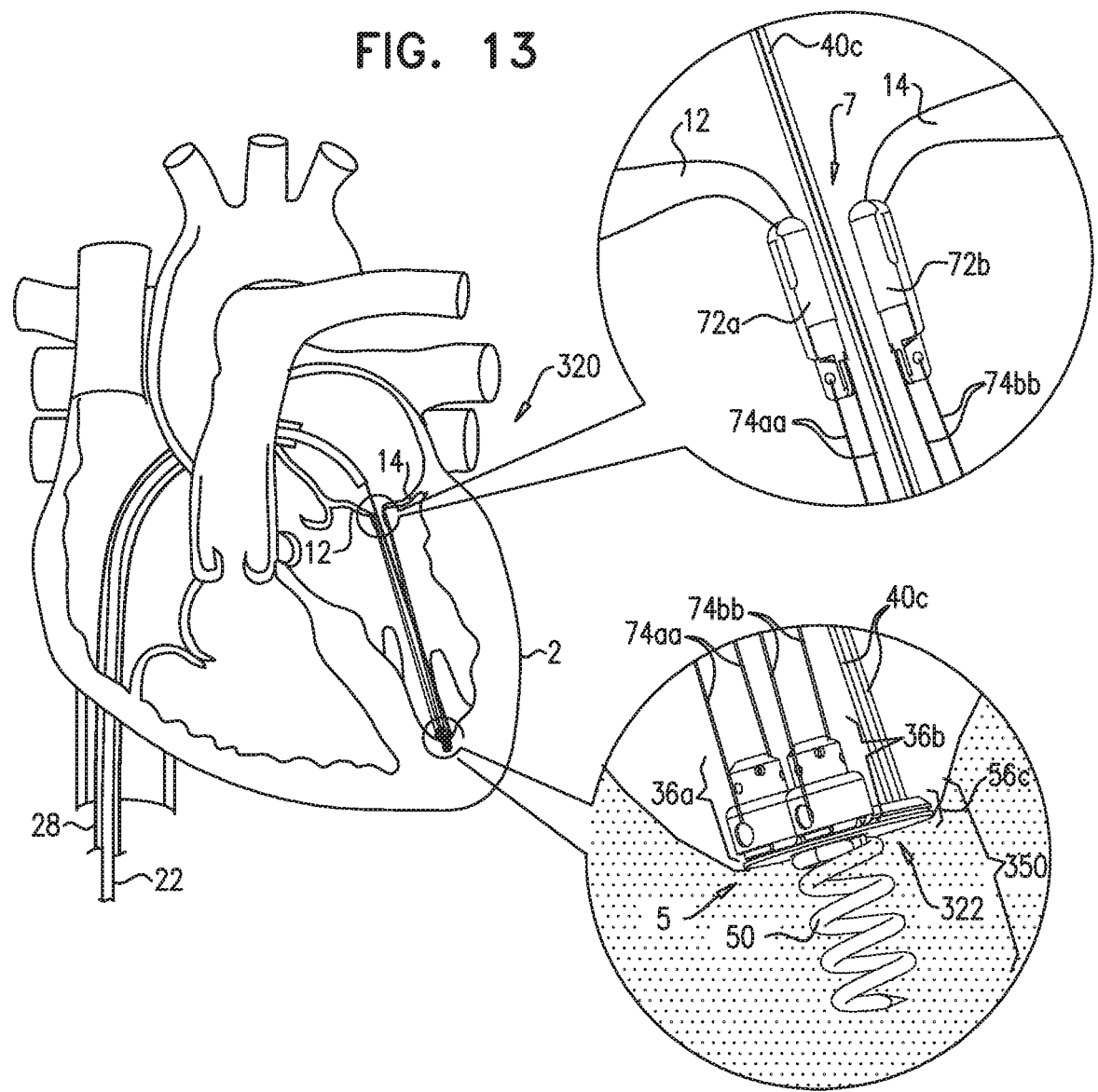
Figure 14:
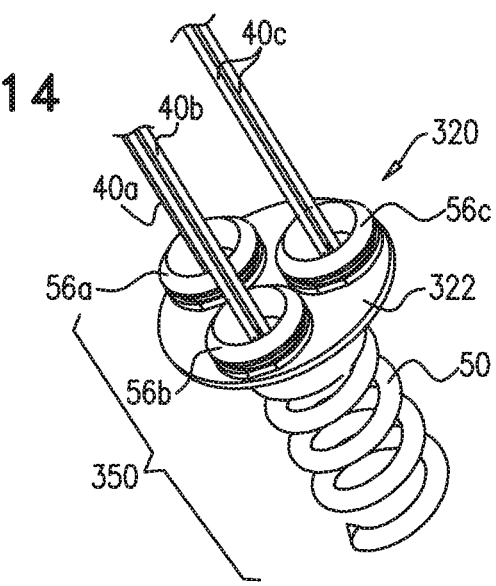

As shown in FIGS. 11-13, first and second spool assemblies 36a and 36b are coupled via respective guide wires 40a and 40b to respective docking stations 56a and 56b. Each spool assembly 36a and 36b has a respective chord 74aa and 74bb extending therefrom (FIG. 13). For example (as shown in FIG. 12), the chord extending from spool assembly 36a has portions 74aa and 74aa' extending from spool assembly 36a. Each chord 74 is coupled to a respective leaflet-engaging element 72. That is, chord 74aa is coupled to leaflet-engaging element 72a, and chord 74bb is coupled to leaflet-engaging element 72b (FIG. 13).

Each leaflet-engaging element 72a and 72b is coupled to leaflets 12 and 14, respectively, and then each spool assembly 36a and 36b is coupled to respective docking stations 56a and 56b, in a manner as described hereinabove. Chords 74aa and 74bb are then adjusted, as described hereinabove. Each chord 74aa and 74bb may be adjusted sequentially or simultaneously.

FIG. 13 shows chords 74aa and 74bb following their adjustment. The relative dispositions of leaflets 12 and 14 are adjusted in conjunction with the adjusting of chords 74aa and 74bb. Typically, leaflets 12 and 14 are drawn together to repair the heart valve.

Figure 15:
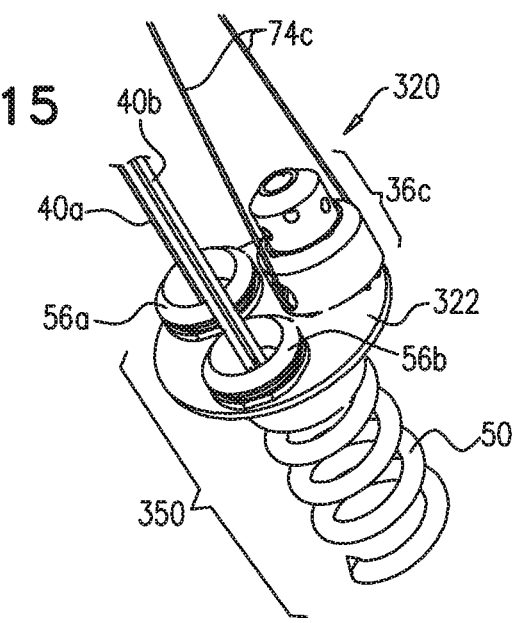

As shown in FIG. 15, a third spool assembly 36c may be coupled to docking station 56c. Chord 74c coupled thereto may be coupled to a third implantation site in heart 2 and subsequently adjusted. FIG. 15 shows third spool assembly 36c coupled to docking station 56c without the presence of the other spool assemblies 36a and 36b, by way of illustration and not limitation.

Figure 16:
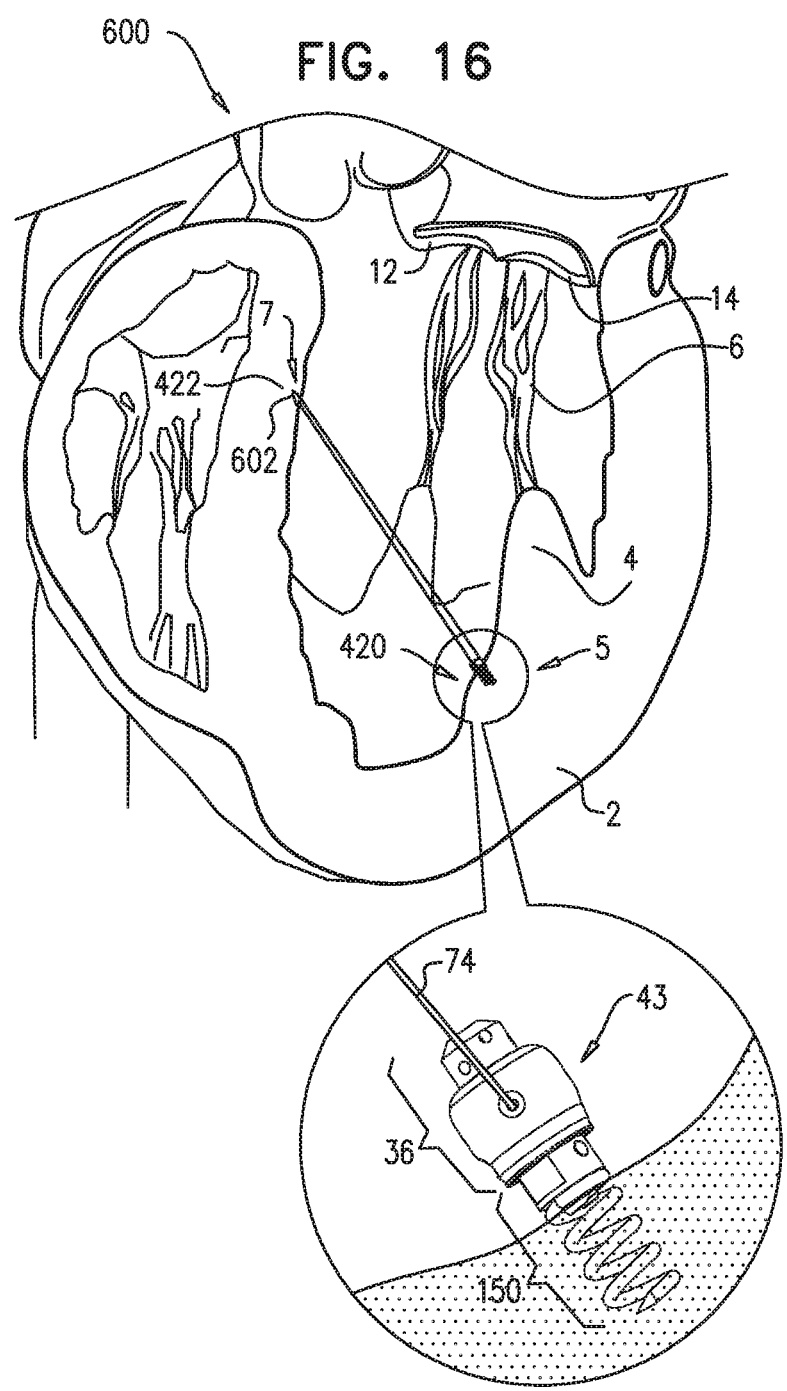
FIG. 16 is a schematic illustration of wall-to-wall adjustment using the docking station, adjustment mechanism, and repair chord, in accordance with some applications of the present invention.

FIG. 16 shows a system 600 for repairing malpositioning of the wall of the ventricle of the patient, in accordance with respective applications of the present invention. System 600 treats a weakened state of heart 2 in which the wall of the left ventricle is malpositioned and weakened. As a result of the malpositioning of the wall of the heart, leaflets 12 and 14 of mitral valve 8 are malpositioned and are distanced from one another (not shown). In order to treat the malpositioning of the heart wall and thereby of leaflets 12 and 14, spool assembly 36 is implanted at a first portion 420 of heart tissue which faces and surrounds the left ventricle of heart 2. First implantation site 5 thus comprises first portion 420 of heart tissue. It is to be noted that first implantation site 5 is at the base of the papillary muscle by way of illustration and not limitation, and that first implantation site 5 may be at a portion of the wall of the heart in a vicinity of the apex of the heart, or at papillary muscle 4. For some applications in which system 600 treats malpositioning of the heart, docking assembly 350 and spool assembly 36 are implanted externally to the ventricle, and chord 74 extends through cardiac tissue and into the ventricle toward implantation site 7.

Spool assembly 36 is implanted via docking assembly 150 at site 5 in a manner as described hereinabove with reference to FIGS. 3-6. As shown, the free ends of chord 74 are coupled to a second portion 422 of heart tissue which faces and surrounds the left ventricle of heart 2. Second implantation site 7 thus comprises second portion 422 of heart tissue, e.g., at the septum, by way of illustration and not limitation. The free ends of longitudinal chord 74 are coupled to the heart tissue using any suitable attachment means 602, e.g., sutures, knotting, or tissue anchors such as helical anchors. Spool 46 of adjustment mechanism 43 is rotated, as described hereinabove, thereby pulling tight chord 74 and thereby reducing a length of chord 74 between first and second implantation sites 5 and 7. In response to the pulling of chord 74, first and second portions 420 and 422 of the heart tissue are pulled toward one another, and a length of chord 74 is adjusted. Consequently, the dimensions of the heart wall are restored to physiological dimensions, and leaflets 12 and 14 are drawn toward one another.

Figure 17:
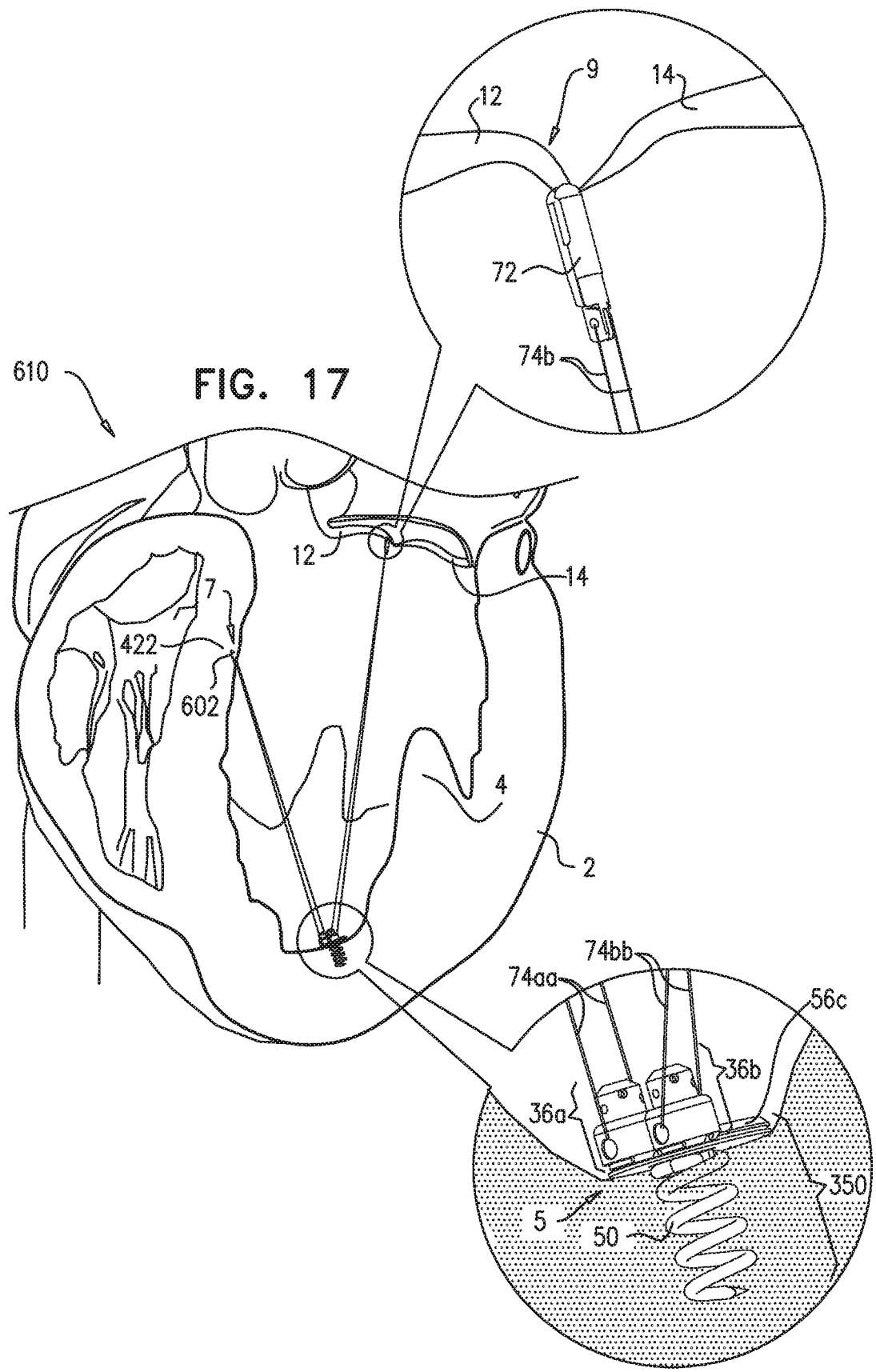
FIG. 17 is a schematic illustration of wall-to-wall adjustment and leaflet adjustment using the plurality of docking stations, the plurality of adjustment mechanisms, and the plurality of repair chords, in accordance with some applications of the present invention.

FIG. 17 shows a system 610 for adjusting both malpositioning of a heart wall of heart 2, and a relative disposition of leaflet 12, in accordance with some applications of the present invention. Multiple-docking-station assembly 350 is implanted at implantation site 5, i.e., a portion of tissue of a heart wall of heart 2 in a vicinity of the apex of heart 2. It is to be noted that implantation site 5 may include any portion of tissue of heart 2, e.g., a portion of tissue at the base of papillary muscle 4, a portion of tissue of papillary muscle 4, or a portion of the free wall of the ventricle. As described hereinabove, first spool assembly 36a is coupled to docking station 56a and adjusts a length of chord 74aa in order to adjust a distance between implantation sites 5 and 7. Second spool assembly 36b is coupled to docking station 56b and adjusts a length of chord 74bb in order to adjust a distance between implantation site 5 a third implantation site 9 (e.g., leaflet 12, as shown). As described hereinabove, chords 74aa and 74bb may be adjusted simultaneously or sequentially. Following the adjusting, implantation sites 7 and 9 are drawn toward multiple-docking-station assembly 350 at implantation site 5. Consequently, the dimensions of the heart wall are restored to physiological dimensions, and leaflets 12 and 14 are drawn toward one another. It is to be noted that although leaflet-engaging element 72 is shown as engaging only leaflet 12, the scope of the present invention includes the engaging of both leaflets 12 and 14 by leaflet-engaging element 72.

It is to be further noted that the scope of the present invention includes the coupling of a third spool assembly to docking station 56c coupled to chord 74c. For such applications, the free end of chord 74c may be coupled to a different portion of cardiac tissue, e.g., leaflet 14.

Figure 18:
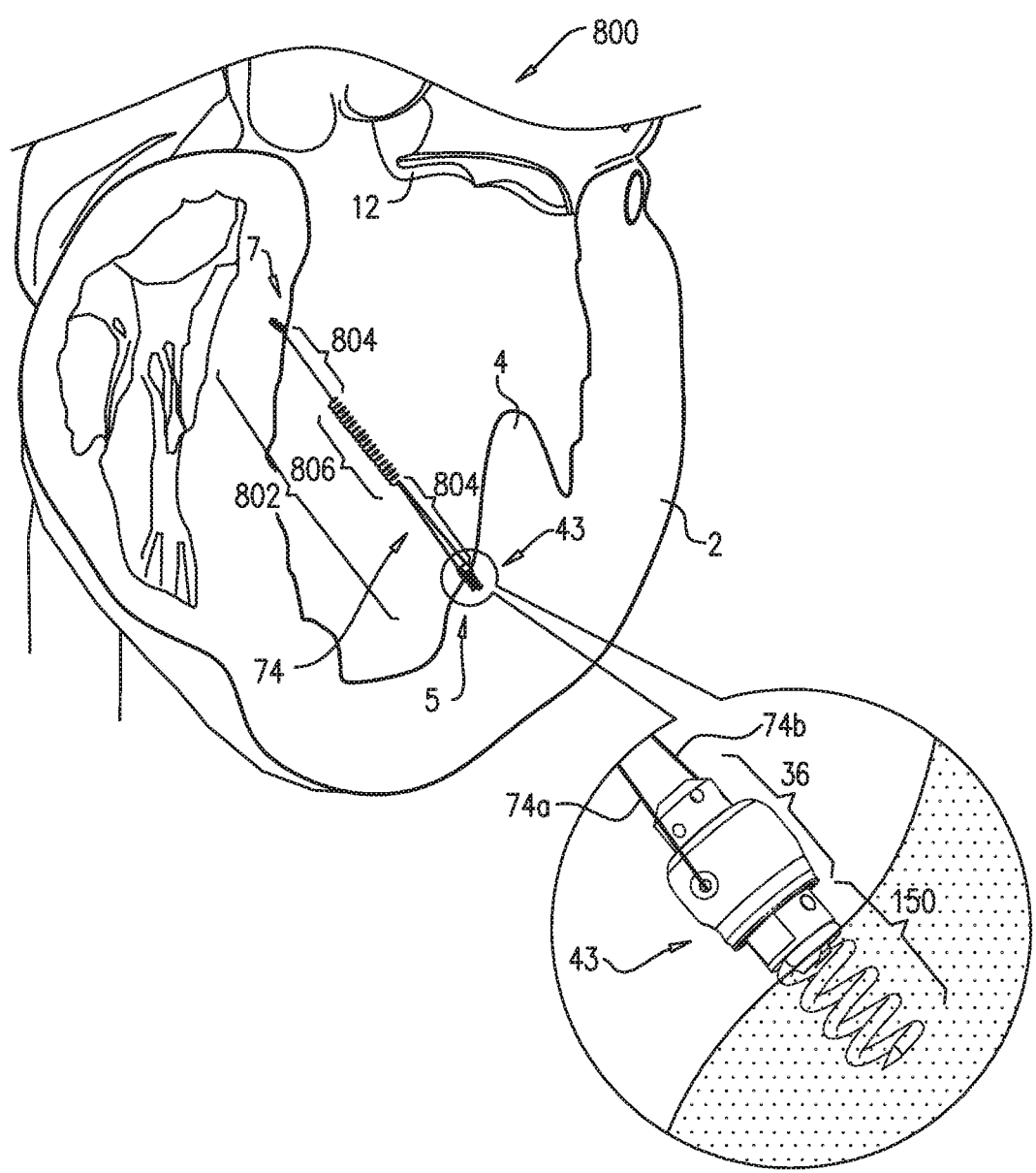
FIG. 18 is a schematic illustration of wall-to-wall adjustment using the docking station, adjustment mechanism, and repair chord, in accordance with some other applications of the present invention.

FIG. 18 is a schematic illustration of a system 800 for adjusting a distance between two portions of a heart wall of the left ventricle of the patient, in accordance with some applications of the present invention. System 800 comprises a tensioning device 802 coupled at a first end thereof to spool assembly 36 at docking assembly 150. In a manner as described hereinabove, spool assembly 36 is implanted at first implantation site 5 in a first portion of tissue of the heart wall that faces and surrounds the ventricular lumen. The free end of tensioning device 802 is attached at second implantation site 7 to a second portion of tissue of the heart wall that faces and surrounds the ventricular lumen. The free end of tensioning device 802 is implanted in heart tissue using a helical anchor by way of illustration and not limitation. For example, the free end of tensioning device 802 may be coupled to second implantation site 7 using sutures, knots, or any tissue anchor known in the art.

Tensioning device 802 comprises a flexible material, e.g., ePTFE or nitinol, and is shaped to define a coiled portion 806 that has a length of between 20 mm and 50 mm and a diameter of between 0.5 mm and 3.0 mm. Tensioning device 802 comprises respective wire/suture portions 804 on either side of coiled portion 806. For such an application, the suture portion 804 that is between spool assembly 36 and coiled portion 806 comprises portions 74a and 74b of chord 74.

As described hereinabove, spool 46 of adjustment mechanism 43 is rotated in order to adjust a distance between first and second implantation sites 5 and 7. As spool 46 is rotated in a first direction thereof, successive portions of chord 74 of suture portion 804 that is disposed adjacently to spool assembly 36 are wrapped around spool 46. Tensioning device 802 is tightened and shortened in response to the wrapping of portion 804 around spool 46. As device 802 is tightened, a force is applied to coiled portion 806 of tensioning device 802. Coiled portion 806 applies a supplemental puling force to help pull the opposing first and second portions of the ventricle wall toward one another. Consequently, the dimensions of the heart wall are restored to physiological dimensions, and leaflets 12 and 14 are drawn toward one another.

Reference is made to FIGS. 16-18. It is to be noted that the scope of the present invention includes the use of systems 600, 610, and 800 for adjusting a distance between any two portions of the heart and not just opposing portions, as described hereinabove. For example, first and second implantation sites 5 and 7 may be on the same side, e.g., the septum, of the wall of the heart.

Figure 19:
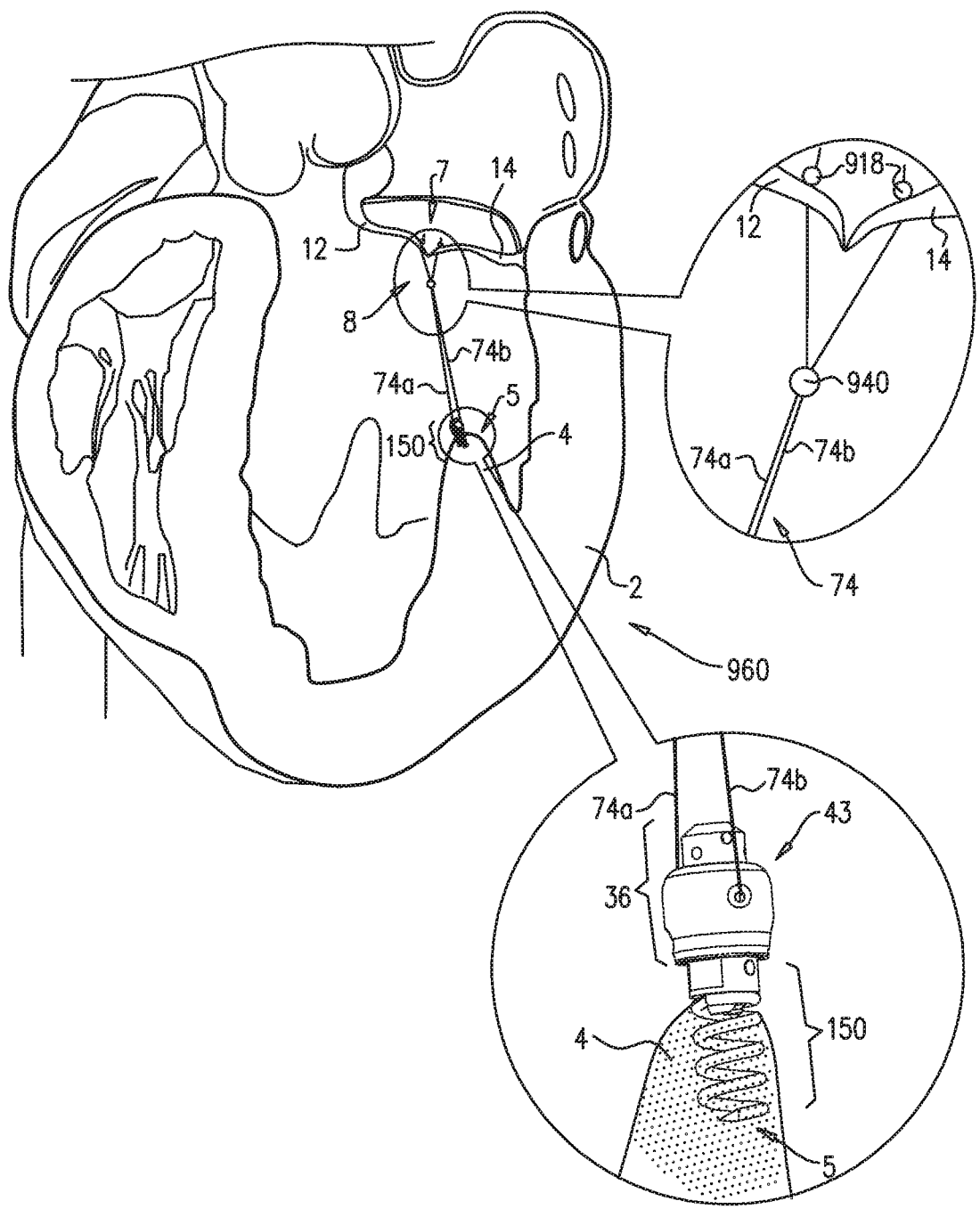
FIGS. 19-20 are schematic illustrations of adjustment of a valve of a patient from a middle portion of the valve, in accordance with some applications of the present invention.

Reference is now made to FIG. 19, which is a schematic illustration of a system 960 for drawing together leaflets 12 and 14 of mitral valve 8 of the patient, in accordance with some applications of the present invention. Spool assembly 36 is implanted via docking assembly 150 in first implantation site 5 at papillary muscle 4 of the left ventricle by way of illustration and not limitation. For example, spool assembly 36 may be implanted in a portion of the heart wall of the ventricle, e.g., the base of the papillary muscle. First and second portions 74a and 74b of chord 74 are coupled (e.g., sutured, anchored, clipped, or locked in place with a crimping bead 918, as shown) to leaflet 12 at an implantation site 902. It is to be noted that portions 74a and 74b may be coupled to leaflets 12 and 14, respectively, using leaflet-engaging elements 72 as described hereinabove.

As described hereinabove, spool 46 of adjustment mechanism 43 is rotated in order to adjust a length of portions 74a and 74b of chord 74. Portions 74a and 74b are pulled tight in response to rotation of spool 46 in a first direction thereof. In response to the pulling of portions 74a and 74b, leaflets 12 and 14 are pulled toward one another in order to restore coaptation to valve 8.

It is to be noted that system 960 may be used on the tricuspid valve.

System 960 further comprises at least one bead 940 that is threaded over portions 74a and 74b of chord 74. The surgeon adjusts the position of the bead along the portions 74a and 74b in order to set the degree to which portions 74a and 74b are free to move with respect to one another. In general, as bead 940 is positioned closer to valve 8, portions 74a and 74b are more constrained in their motion with respect to one another, and leaflets 12 and 14 are drawn closer together. For some applications of the present invention, bead 940 comprises a fixation mechanism (e.g., a crimping mechanism), which is configured to fix the bead to portions 74a and 74b of chord 74 once bead 940 has been positioned at a desire location along portions 74a and 74b.

Figure 20:
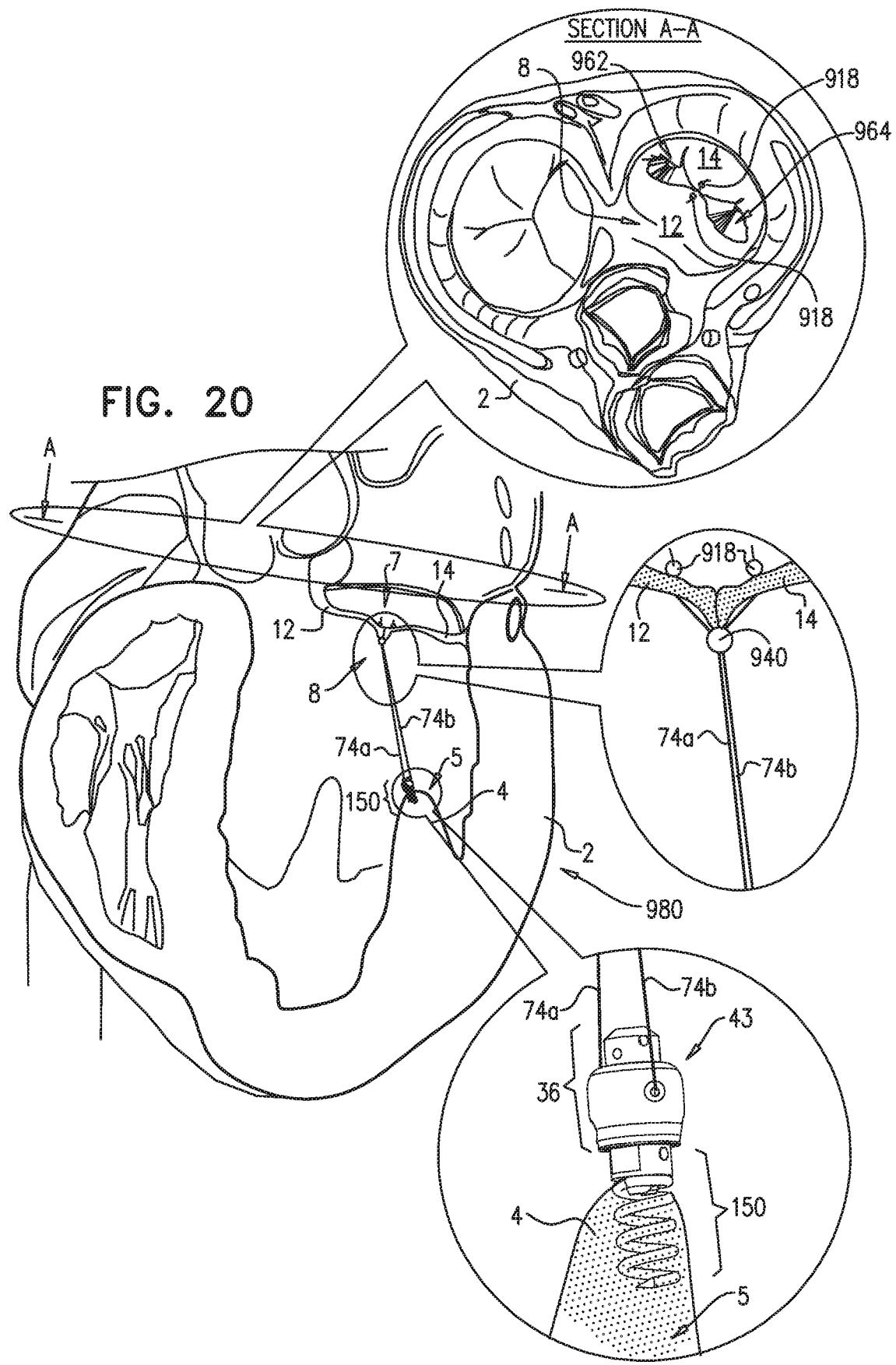

FIG. 20 shows a system 980 that is similar to system 960 as described with reference to FIG. 19, with the exception that bead 940 is pulled by the operating physician to the ventricular surface of a middle portion of valve 8, in accordance with some applications of the present invention. Such pulling of bead 940 to the ventricular surface creates a bridge between leaflets 12 and 14, e.g., as an Alfieri stitch, or edge-to-edge repair. Portions 74a and 74b are then adjusted in order to pull together the middle portion of mitral valve 8, as shown in Section A-A. The firm coupling of leaflets 12 and 14 prevents prolapsing of leaflets 12 and 14, facilitates coaptation of leaflets 12 and 14, and creates orifices 962 and 964 (section A-A) in mitral valve 8 so as to facilitate blood flow from the atrium to the ventricle. Additionally, the adjusting of portions 74a and 74b of chord 74 draws downward leaflets 12 and 14 and adjusts chord 74 such that it functions as an artificial chordea tendinea.

Reference is now made to FIGS. 19 and 20. It is to be noted that although docking assembly 150 is shown, multiple-docking-station assembly 350 as described hereinabove, may be implanted at implantation site 5. For such an application, two or more spool assemblies 36 may be coupled to multiple-docking-station assembly 350, and any number of chords 74 extending from each spool assembly 36 may be coupled to leaflets 12 and 14 at any suitable location thereof. The lengths of chords 74 are then adjusted by spool assemblies 36 in order to pull leaflets 12 and 14 together.

Figure 21:
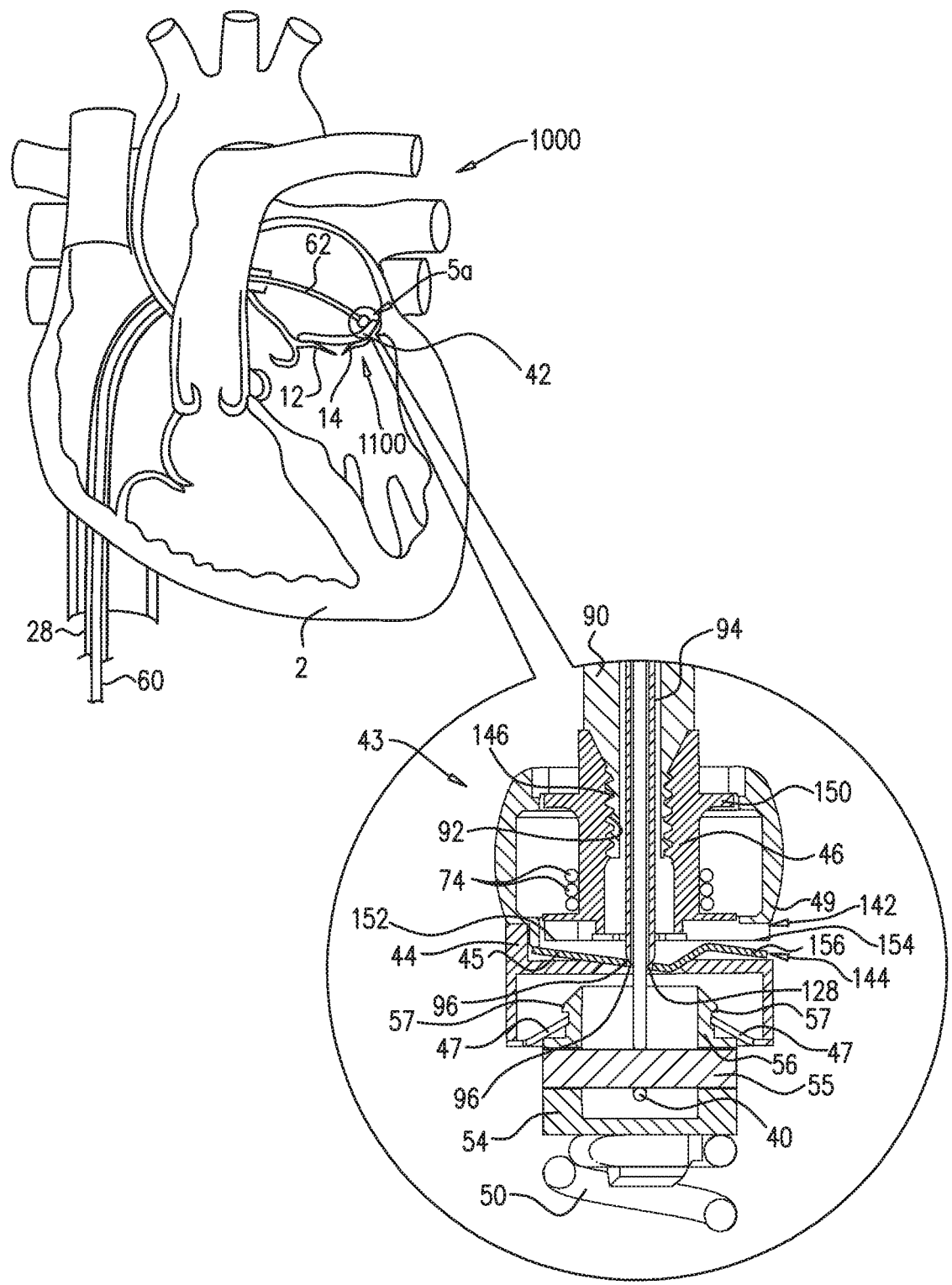
FIG. 21 is a schematic illustration of the tissue-engaging element and the docking station of FIGS. 1 and 2 being used to facilitate implantation of an implant at a cardiac valve, in accordance with some applications of the present invention.

Reference is now made to FIG. 21, which is a schematic illustration of a system 1000 comprising docking assembly 150 for implantation at an implantation site 5a that includes an annulus 1100 of a cardiac valve of the patient, in accordance with some applications of the present invention. It is to be noted that the mitral valve is shown by way of illustration and not limitation, and that system 1000 can be used on any other cardiac valve of the patient, e.g., the tricuspid valve, the pulmonary valve, and the aortic valve. System 1000 comprises docking assembly 150 and the guide member coupled thereto (e.g., guide wire 40), as described hereinabove with reference to FIGS. 1-2.

For some applications in which docking assembly 150 is implanted at the annulus of the cardiac valve, implant 42 configured to be coupled to docking assembly 150 comprises an annuloplasty ring structure (e.g., a full annuloplasty ring or a partial annuloplasty ring). Typically, the annuloplasty ring structure comprises adjustment mechanism 43. It is to be noted, however, that the annuloplasty ring structure configured to be coupled to docking assembly 150 may be provided independently of adjustment mechanism 43. That is, any suitable annuloplasty ring structure may be coupled to docking assembly 150. For such applications, the annuloplasty ring structure is slid along guide wire 40 toward docking assembly 150.

For other applications in which docking assembly 150 is implanted at the annulus of the cardiac valve, implant 42 configured to be coupled to docking assembly 150 comprises a prosthetic valve or a support structure for coupling a prosthetic valve thereto. For some applications, the support structure comprises adjustment mechanism 43. It is to be noted, however, that the support structure configured to be coupled to docking assembly 150 may be provided independently of adjustment mechanism 43. That is, any suitable support structure or prosthetic valve may be coupled to docking assembly 150. For such applications, the support structure or prosthetic valve is slid along guide wire 40 toward docking assembly 150.

Figure 22:
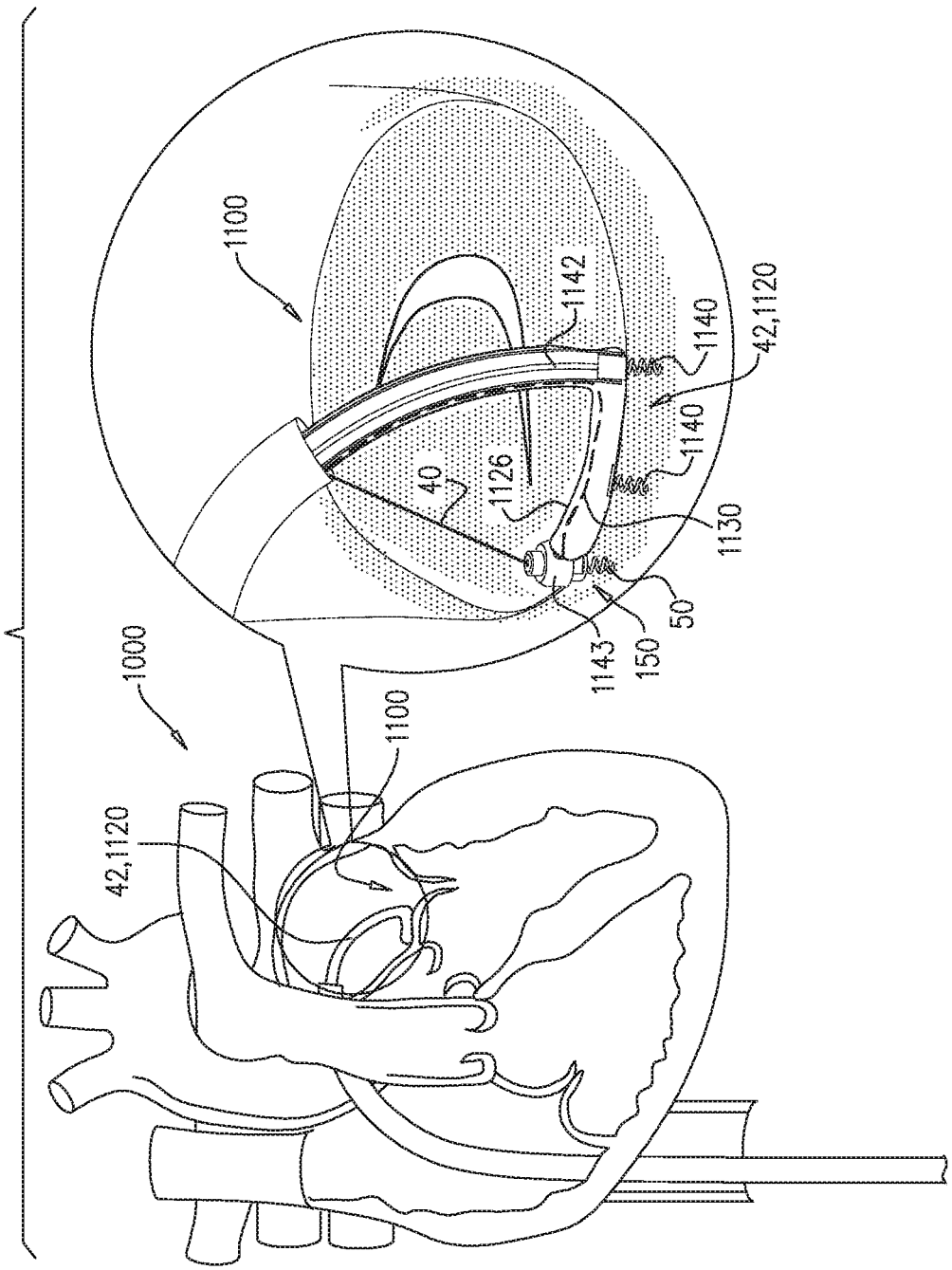
FIG. 22 is a schematic illustration of the tissue-engaging element and the docking station of FIGS. 1 and 2 being used to facilitate implantation of an annuloplasty ring at a cardiac valve, in accordance with some applications of the invention.

Reference is made to FIG. 22, which is a schematic illustration of system 1000 being used to facilitate implantation of implant 42, comprising an annuloplasty ring 1120, at annulus 1100 of a cardiac valve, in accordance with some applications of the invention. It is to be noted that the mitral valve is shown by way of illustration and not limitation, and that system 1000 can be used on any other cardiac valve of the patient, e.g., the tricuspid valve, the pulmonary valve, and the aortic valve. It is to be noted that annuloplasty ring 1120 is shown as a partial annuloplasty ring by way of illustration and not limitation, and that annuloplasty ring 1120 may comprise a full annuloplasty ring. Docking assembly 150 is advanced to the annulus, and tissue anchor 50 is anchored to tissue in the vicinity of the annulus (e.g., to tissue of the annulus). For applications in which tissue anchor 50 comprises a helical tissue anchor, the anchor is typically coupled to the tissue by rotating the entire docking assembly 150 (e.g., using a delivery tool, such as delivery tool 30, described hereinabove with reference to FIGS. 1-2, mutatis mutandis). As described hereinabove (e.g., with reference to FIG. 2), a guide member (e.g., guide wire 40) is left behind, coupled to docking assembly 150 (e.g., to docking station 56 thereof).

Subsequently, and as shown in FIG. 22, annuloplasty ring 1120 is advanced along guide wire 40 toward annulus 1100 and docking assembly 150. Typically, annuloplasty ring 1120 is shaped to define a channel therethrough (e.g., between an upper surface and a lower surface of the annuloplasty ring), within which guide wire 40 is configured to be disposed, and the annuloplasty ring is slid over the guide wire. For some applications, and as shown in FIG. 22, annuloplasty ring 1120 comprises an adjustable annuloplasty ring that comprises an adjustment mechanism 1143, configured to adjust the annuloplasty ring (e.g., as described hereinbelow). For some such applications, adjustment mechanism 1143 is shaped to define the channel within which guide wire 40 is configured to be disposed.

Typically, adjustment mechanism 1143 comprises adjustment mechanism 43 and/or spool assembly 36, described hereinabove. Further typically, annuloplasty ring 1120 comprises a sleeve 1126 that defines a lumen therethrough, and a flexible longitudinal member 1130, disposed at least in part within the lumen of the sleeve, and adjustment mechanism 1143 is configured to adjust the length of the sleeve (e.g., the diameter of the annuloplasty ring) by adjusting the length of the flexible longitudinal member. For some applications, flexible longitudinal member 1130 is coupled to and adjusted by adjustment mechanism 1143, in a similar manner to that in which chord 74 is coupled to and adjusted by adjustment mechanism 43, described hereinabove.

Once annuloplasty ring 1120 reaches docking assembly 150, the annuloplasty ring is locked to the docking assembly as described hereinabove (e.g., with reference to FIG. 6), mutatis mutandis. That is, a coupling defined by the annuloplasty ring is locked to a coupling defined by the docking assembly, typically by the couplings being pushed toward and/or into each other.

For some applications, additional anchors are subsequently used to couple other portions of annuloplasty ring 1120 to other portions of tissue in the vicinity of annulus 1100. For example, and as shown in FIG. 22, annuloplasty ring 1120 may comprise a partial annuloplasty ring that comprises sleeve 1126, and successive portions of sleeve 1126 may be placed on annulus 1100, and anchored to the annulus using a plurality of successive anchors 1140, deployed using a deployment manipulator 1142, from within the lumen of the sleeve, through the wall of the sleeve, and into the annulus. For some such applications, docking assembly 150 is used to guide and anchor a first portion of the annuloplasty ring to a first anchoring site of the annulus, and successive anchors 1140 are subsequently used to anchor other portions of the annuloplasty ring.

For some applications, a plurality of docking assemblies 150 and a plurality of guide wires 40 are used to advance and lock a plurality of portions of annuloplasty ring 1120 to the tissue. For some such applications, annuloplasty ring comprises a plurality of adjustment mechanisms 1143 disposed around the length of sleeve 1126 (e.g., to adjust the length of different portions of the sleeve), and each of the adjustment mechanisms is advanced over a respective guide wire 40 and locked to a respective docking station of a respective docking assembly.

It is to be noted that the locking of annuloplasty ring 1120 to docking assembly 150 is performed sutureles sly.

For some applications of the present invention, systems 20, 220, 320, 600, 610, 800, 960, 980, and 1000 are used to treat an atrioventricular valve other than the mitral valve, i.e., the tricuspid valve. For these applications, systems 20, 220, 320, 600, 610, 800, 960, 980, and 1000 described hereinabove as being placed in the left ventricle are instead placed in the right ventricle.

It is to be noted that the scope of the present invention includes the use of systems 20, 220, 320, 600, 610, 800, 960, 980, and 1000 on other cardiac valves, such as the pulmonary valve or the aortic valve.

It is to be further noted that the scope of the present invention includes the use of systems 20, 220, 320, 600, 610, 800, 960, 980, and 1000 on other tissue other than cardiac tissue, e.g., gastric tissue or any other suitable tissue or organ.

For some applications, techniques described herein are practiced in combination with techniques described in one or more of the references cited in the Background section of the present patent application.

Additionally, the scope of the present invention includes applications described in the following applications, which are incorporated herein by reference. In an application, techniques and apparatus described in one or more of the following applications are combined with techniques and apparatus described herein:

PCT Publication WO 2006/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as WO 2008/068756;

U.S. patent application Ser. No. 11/950,930 to Gross et al., entitled, "Segmented ring placement," filed on Dec. 5, 2007, which published as US Patent Application Publication 2008/0262609 (now U.S. Pat. No. 8,926,695);

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as 2010/0161047 (now U.S. Pat. No. 8,241,351);

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as 2010/0161041 (now U.S. Pat. No. 8,147,542);

U.S. patent application Ser. No. 12/437,103 to Zipory et al., entitled, "Annuloplasty ring with intra-ring anchoring," filed on May 7, 2009, which published as 2010/0286767 (now U.S. Pat. No. 8,715,342);

PCT Patent Application PCT/IL2009/000593 to Gross et al., entitled, "Annuloplasty devices and methods of delivery therefor," filed on Jun. 15, 2009, which published as WO 2010/004546;

U.S. patent application Ser. No. 12/548,991 to Maisano et al., entitled, "Implantation of repair chords in the heart," filed on Aug. 27, 2009, which published as 2010/0161042 (now U.S. Pat. No. 8,808,368);

U.S. patent application Ser. No. 12/608,316 to Miller et al., entitled, "Tissue anchor for annuloplasty ring," filed on Oct. 29, 2009, which published as 2011/0106247 (now U.S. Pat. No. 8,277,502);

PCT Patent Application PCT/IL2009/001209 to Cabiri et al., entitled, "Adjustable annuloplasty devices and mechanisms therefor," filed on Dec. 22, 2009, which published as WO 2010/073246;

U.S. patent application Ser. No. 12/689,635 to Zipory et al., entitled, "Over-wire rotation tool," filed on Jan. 19, 2010, which published as 2010/0280604 (now U.S. Pat. No. 8,545,553);

U.S. patent application Ser. No. 12/689,693 to Hammer et al., entitled, "Application Deployment techniques for annuloplasty ring," filed on Jan. 19, 2010, which published as 2010/0280605 (now U.S. Pat. No. 8,911,494);

U.S. patent application Ser. No. 12/706,868 to Miller et al., entitled, "Actively-engageable movement-restriction mechanism for use with an annuloplasty structure," filed on Feb. 17, 2010, which published as 2010/0211166 (now U.S. Pat. No. 8,353,956); and/or U.S. patent application Ser. No. 12/795,026 to Miller et al., entitled, "Apparatus for guide-wire based advancement of a rotation assembly," filed on Jun. 7, 2010, which published as 2011/0106245 (now U.S. Pat. No. 8,940,042).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system for use with a heart of a subject, the system comprising:
    a tissue-engaging element having a distal portion configured to engage a portion of tissue of the heart;
    a guide member reversibly coupled to the tissue-engaging element;
    an elongate implant having a distal end and a proximal end, at least the distal end being slidably coupled to the guide member; and
    a tool, slidable along the guide member distally toward the tissue-engaging element such that sliding of the tool along the guide member distally toward the tissue-engaging element, while the tool is coupled to at least the distal end of the elongate implant, slides at least the distal end of the elongate implant toward the tissue-engaging element;
    wherein the tool is configured to decouple the guide member from the tissue-engaging element.

2. The system according to claim 1, wherein the tool is configured to couple the distal end of the elongate implant to the tissue-engaging element.

3. The system according to claim 1, further comprising a cap that is shaped to define an opening through which the guide member is slidable, wherein at least the distal end of the elongate implant is slidably coupled to the guide member via the cap.

4. The system according to claim 1, wherein the tool is configured to couple a proximal end of the elongate implant to a valve leaflet of the heart.

5. The system according to claim 4, further comprising a leaflet-engaging element coupled to a proximal end of the elongate implant, and wherein:
    the tool comprises a holder, reversibly coupled to the leaflet-engaging element,
    the tool is configured to couple the proximal end of the elongate implant to the valve leaflet by coupling the leaflet-engaging element to the leaflet.

6. The system according to claim 1, further comprising an adjustment mechanism that is coupled to the distal end of the elongate implant, and is configured to adjust a tension of the elongate implant upon actuation of the adjustment mechanism.

7. The system according to claim 6, wherein:
    the tool is coupled to a proximal end of the elongate implant, and is configured to couple the proximal end of the elongate implant to a valve of the heart, and
    while (i) the tool is coupled to the distal end of the elongate implant, and to the proximal end of the elongate implant, and (ii) the elongate implant is entirely within the heart, the tool is configured to adjust a distance between the distal end of the elongate implant and the proximal end of the elongate implant, independently of actuation of the adjustment mechanism.

8. The system according to claim 6, wherein the tool is reversibly couplable to the distal end of the elongate implant by being reversibly coupled to the adjustment mechanism.

9. The system according to claim 8, wherein the tool is configured to actuate the adjustment mechanism.

10. The system according to claim 6, wherein the adjustment mechanism:
comprises a rotatable structure disposed within a housing, and coupled to the elongate implant, and
is configured to adjust the tension of the elongate implant by rotation of the rotatable structure with respect to the housing.

11. The system according to claim 10, wherein the rotatable structure is rotatable bidirectionally with respect to the housing.

12. The system according to claim 10, wherein the adjustment mechanism comprises a locking mechanism configured to reversibly inhibit rotation of the rotatable structure with respect to the housing.

13. The system according to claim 1, wherein the tool is configured to couple the distal end of the elongate implant to the tissue-engaging element, and to subsequently decouple the guide member from the tissue-engaging element while the elongate implant remains coupled to the tissue-engaging element.

14. The system according to claim 1, wherein the tool is a first delivery tool, and the system further comprises a second delivery tool, configured to advance the tissue-engaging element to the heart, and to secure the tissue-engaging element to the portion of tissue.

15. The system according to claim 14, further comprising a sheath that is transluminally and transseptally advanceable into a left atrium of the heart, wherein:
the second delivery tool is configured to advance the tissue-engaging element, coupled to the guide member, through the sheath to the heart,
subsequent to securing the tissue-engaging element to the portion of the tissue, the second delivery tool is disengageable from the tissue-engaging element and removable from the subject,
subsequent to removal of the second delivery tool from the subject, the first delivery tool is slidable, within the sheath, along the guide member distally toward the tissue-engaging element, while (i) the tool is coupled to at least the distal end of the elongate implant, and (ii) the guide member remains coupled to the tissue-engaging element.

16. The system according to claim 1, wherein:
the portion of tissue faces a ventricle of the heart,
the distal portion of the tissue-engaging element is configured to engage the portion of tissue that faces the ventricle of the heart, and
the tool is slidable along the guide member distally toward the tissue-engaging element while (i) the tool is coupled to at least the distal end of the elongate implant, and (ii) the guide member is coupled to the tissue-engaging element, such that sliding of the tool along the guide member distally toward the tissue-engaging element while (i) the tool is coupled to at least the distal end of the elongate implant, (ii) the guide member is coupled to the tissue-engaging element, and (iii) the distal portion of the tissue-engaging element is engaged with the portion of tissue that faces the ventricle of the heart, slides at least the distal end of the elongate implant toward the portion of tissue that faces the ventricle of the heart.

17. The system according to claim 16, wherein:
the portion of tissue is a papillary muscle of the heart,
the distal portion of the tissue-engaging element is configured to engage the papillary muscle, and
the tool is slidable along the guide member distally toward the tissue-engaging element while (i) the tool is coupled to at least the distal end of the elongate implant, and (ii) the guide member is coupled to the tissue-engaging element, such that sliding of the tool along the guide member distally toward the tissue-engaging element while (i) the tool is coupled to at least the distal end of the elongate implant, (ii) the guide member is coupled to the tissue-engaging element, and (iii) the distal portion of the tissue-engaging element is engaged with the papillary muscle, slides at least the distal end of the elongate implant toward the papillary muscle.

18. The system according to claim 1, wherein the tissue-engaging element is an anchor, and the distal portion of the tissue-engaging element is helical and configured to be corkscrewed into the portion of tissue.

19. The system according to claim 1, further comprising a sheath that is transluminally and transseptally advanceable into a left atrium of the heart, wherein the tool is slidable, within the sheath, along the guide member distally toward the tissue-engaging element.

20. A system for use with a heart of a subject, the system comprising:
a tissue-engaging element having a distal portion configured to engage a portion of tissue of the heart;
a guide member reversibly coupled to the tissue-engaging element;
an elongate implant having a distal end and a proximal end, at least the distal end being slidably coupled to the guide member;
a leaflet-engaging element coupled to a proximal end of the elongate implant; and
a tool, slidable along the guide member distally toward the tissue-engaging element such that sliding of the tool along the guide member distally toward the tissue-engaging element, while the tool is coupled to at least the distal end of the elongate implant, slides at least the distal end of the elongate implant toward the tissue-engaging element;
wherein the tool is configured to couple a proximal end of the elongate implant to a valve leaflet of the heart;
wherein the tool comprises a holder, reversibly coupled to the leaflet-engaging element, and
wherein the tool is configured to couple the proximal end of the elongate implant to the valve leaflet by coupling the leaflet-engaging element to the leaflet.

* * * * *